US 6,627,067 B1

(12) United States Patent
Branton et al.

(10) Patent No.: US 6,627,067 B1
(45) Date of Patent: Sep. 30, 2003

(54) MOLECULAR AND ATOMIC SCALE EVALUATION OF BIOPOLYMERS

(75) Inventors: Daniel Branton, Lexington, MA (US); Jene A. Golovchenko, Lexington, MA (US); Timothy J. Denison, Andover, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 426 days.

(21) Appl. No.: 09/602,650

(22) Filed: Jun. 22, 2000

Related U.S. Application Data
(60) Provisional application No. 60/140,201, filed on Jun. 22, 1999.

(51) Int. Cl.[7] .......................... G01N 27/327; C12M 3/00
(52) U.S. Cl. ................ 205/778; 204/403.06; 435/287.2
(58) Field of Search ....................... 204/403.06, 403.08, 204/403.07; 205/777.5, 778; 435/287.2, 287.1

(56) References Cited

U.S. PATENT DOCUMENTS

| | | | |
|---|---|---|---|
| 4,874,499 A | 10/1989 | Smith et al. | 204/403.02 |
| 5,221,447 A * | 6/1993 | Hjerten | 427/235 |
| 5,356,776 A * | 10/1994 | Kambara et al. | 435/6 |
| 5,376,878 A | 12/1994 | Fisher | 324/471.4 |
| 5,612,179 A | 3/1997 | Simons | |
| 5,795,782 A | 8/1998 | Church et al. | 436/2 |
| 5,833,826 A * | 11/1998 | Nordman | 204/452 |
| 6,015,714 A | 1/2000 | Baldarelli et al. | 436/2 |
| 6,054,035 A * | 4/2000 | Kambara | 204/601 |
| 6,156,502 A | 12/2000 | Beattie | |
| 6,190,865 B1 | 2/2001 | Jendrisak et al. | |
| 6,203,993 B1 | 3/2001 | Shuber et al. | |
| 6,214,545 B1 | 4/2001 | Dong et al. | |
| 6,221,603 B1 | 4/2001 | Mahtani | |
| 6,238,866 B1 | 5/2001 | Yeh et al. | |
| 6,355,420 B1 | 3/2002 | Chan | |
| 6,362,002 B1 | 3/2002 | Denison et al. | |
| 6,403,311 B1 | 6/2002 | Chan | |
| 6,528,258 B1 | 3/2003 | Russell | |
| 2002/0039737 A1 | 4/2002 | Chan et al. | |
| 2002/0081744 A1 | 6/2002 | Chan et al. | |
| 2002/0119455 A1 | 8/2002 | Chan | |

FOREIGN PATENT DOCUMENTS

| | | |
|---|---|---|
| DE | 3028569 A1 | 2/1982 |
| GB | 2 232 769 A | 12/1990 |
| WO | WO 94/25862 | 11/1994 |
| WO | WO 98/35012 | 8/1998 |
| WO | WO 00/09757 | 2/2000 |

OTHER PUBLICATIONS

Bensimon et al., "Alignment and Sensitive Detection of DNA by a Moving Interface," Science, 265, 1994 (pp. 2096–2098) Sep. 30, 1994.

Ghadiri et al., "Artificial Transmembrane Ion Channels from Self–Assembling Peptide Nanotubes," Nature 369, 1994 (pp. 301–304) May 26, 1994.

(List continued on next page.)

Primary Examiner—Nam Nguyen
(74) Attorney, Agent, or Firm—Hale and Dorr LLP

(57) ABSTRACT

A method for evaluating a polymer molecule including linearly connected monomer residues includes providing a polymer molecule in a liquid, contacting the liquid with an insulating solid-state membrane having a detector capable of detecting polymer molecule characteristics, and causing the polymer molecule to traverse a limited region of the solid-state membrane so that monomers of the polymer molecule traverse the limit region in sequential order, whereby the polymer molecule interacts linearly with the detector and data suitable to determine polymer molecule characteristics are obtained. The limited region may be defined by a nanometer-sized aperture in the membrane.

76 Claims, 18 Drawing Sheets

OTHER PUBLICATIONS

Lakey et al., "The Voltage–Dependent Activity of Escherichia Coli Porins in Different Planar Bilayer Reconstitutions," *Eur. J. Biochem.* 186, 1989 (pp. 303–308).

Neher et al., "Single–Channel Currents Recorded from Membrane of Denervated Frog Musclue Fibres," *Nature* 260, 1976 (pp. 799–801).

Sigworth et al., "Open Channel Noise: III. High Resolution Recordings Show Rapid Current Fluctuations in Gramicidin A and Four Chemical Analogues," *J. Biophys.* 52, 1987 (pp. 1055–1064).

Auld et al., "A Neutral Amino Acid Change in Segment IIS4 Dramatically Alters the Gating Properties of the Voltage–Dependent Sodium Channel" *Proc. Natl. Acad. Sci. USA* 87:323–327 (Jan. 1990).

Bezrukov et al., "Counting Polymers Moving Through a Single Ion Channel" *Nature* 370:279–281(Jul. 1994).

DeBlois et al., "Electrokinetic Measurements with Submicron Particles and Pores by the Resistive Pulse Technique" *Journal of Colloid and Interface Science* 61:323–335 (Sep. 1977).

Hamill et al., "Improved Patch–Clamp Techniques for High–Resolution Current Recording from Cells and Cell–Free Membrane Patches" *Pflügers Archiv* 391:85–100 (Aug. 1981).

Heinemann and Sigworth "Open Channel Noise IV: Estimation of Rapid Kinetics of Formamide Block in Gramicidin A Channels" *Biophysical Journal* 54:757–764 (Oct. 1988).

Heinemann and Sigworth "Open Channel Noise V: Fluctuating Barriers to Ion Entry in Gramicidin A Channels" *Biophysical Journal* 57:499–514 (Mar. 1990).

Henry et al., "Blockade of a Mitochondrial Cationic Channel by an Addressing Peptide: An Electrophysiological Study" *J. Membrane Biol.* 112:139–147 (Dec. 1989).

Kasianowicz et al., "Characterization of Individual Polynucleotide Molecules Using a Membrane Channel" *Proc. Natl. Acad. Sci. USA* 93:13770–13773 (Nov. 1996).

Wonderlin et al., "Optimizing Planar Lipid Bilayer Single–Channel Recordings for High Resolution with Rapid Voltage Steps" *Biophysical Journal* 58:289–297 (Aug. 1990).

Yager "Biosensors from Membrane Proteins Reconstituted in Polymerized Lipid Bilayers" United States Statutory Invention Registration, Reg. No. H201, (Jan. 6, 1987).

\* cited by examiner

LONGITUDINAL CONDUCTANCE
MEASUREMENT

TRANSVERSE CONDUCTANCE
MEASUREMENT

US 6,627,067 B1

MOLECULAR AND ATOMIC SCALE EVALUATION OF BIOPOLYMERS

CROSS REFERENCE TO RELATED APPLICATIONS

This application claims priority under 35 U.S.C. §119(e) to U.S. Ser. No. 60/140,201 entitled "Method for Producing and Controlling the Size of Holes in Membranes, with Application to Voltage-Controlled Nanopore Sequencing of DNA and Other Polymers," filed Jun. 22, 1999, which is incorporated by reference. This application is related to application Ser. No. 09/599,137, entitled, "Control of Solid State Dimensional Features," filed on even date herewith (Jun. 22, 2000), now U.S. Pat. No. 6,464,842, and incorporated by reference.

STATEMENT AS TO FEDERALLY SPONSORED RESEARCH

This invention was made with United States Government support under DARPA grant number N65236-99-1-5407. The Government has certain rights in this invention.

BACKGROUND OF THE INVENTION

Rapid, reliable and inexpensive characterization of polymers, particularly nucleic acids, has become increasingly important. A high-throughput device that can probe and directly read, at the single-molecule level, hybridization state, base stacking, and sequence of a cell's key biopolymers such as DNA, RNA and even proteins, will dramatically alter the pace of biological development.

Church et al. in U.S. Pat. No. 5,795,782 recently reported that a voltage bias could drive single-stranded charged polynucleotides through a 1–2 nanometer transmembrane channel in a lipid bilayer. Data in the form of variations in channel ionic current provide insight into the characterization and structure of biopolymers at the molecular and atomic levels. The passage of an individual strand through the channel could be observed as a transient decrease in ionic current. Experiments using biological membranes and pores have demonstrated extraordinary electronic sensitivity to the structure of translocating molecules. See, U.S. Pat. No. 5,795,782 and Kasianowicz et al. ("Characterization of individual polynucleotide molecules using a membrane channel", Proc. Natl. Acad. Sci. 93:13770 (November 1996)).

This is demonstrated in FIG. 1, in which a lipid bilayer 10 having a α-hemolsin channel 12 therein is shown. A *Staphylococcus aureus* α-hemolsin channel is used because its inner diameter has a limiting aperture of 1.5 nm, which is adequate to admit single-stranded DNA. The layer separates two solution-filled compartments 14, 16 in which ions are free to migrate through the channel 12 in response to an applied voltage. The unobstructed ionic current 18 is illustrated in the upper channel 12 of FIG. 1. If negatively charged molecules, such as DNA, are placed in compartment 14 and a negative bias is applied, the molecules are pulled one at a time into, and through, the channel. The ionic current is reduced as a polymeric molecule 17 traverses the channel from the cis to the trans compartment, as is illustrated in the lower channel 19 of the figure. The number of transient decreases of ionic current per unit time (the blockade rate) is proportional to the concentration of polymer in the source solution. Furthermore, the duration of each blockade is proportional to polymer length.

FIG. 2 is an example of actual current traces obtained using a lipid membrane containing an *S. aureus* α-hemolsin channel. The voltage applied across the bilayer (−120 mV) produces a current of ions that flow through the channel. After adding DNA, transient reductions in current are evident in the trace (FIG. 2A). The time it takes for the DNA to be drawn through the channel (FIG. 2B), effectively measures the length of a DNA molecule (here, 1300 $\mu$s corresponding to a 1,060 nt polymer). The extent to which ionic flow is reduced (here, from about 120 pA to 15 pA) reflects the physical properties of the nucleotides in the polymer.

While a protein channel has demonstrated the ability to identify characteristics of polynucleotides, attaining the resolution and precision needed to achieve error-free sequencing of individual monomers has proved to be a challenge. For example, it has been demonstrated that detection sensitivity extends along the entire length of the α-hemolsin protein channel, and this despite the sharp limiting asperity of 1.5 nm at its neck. The interactions of multiple monomer units along its entire length contribute to the blocked current magnitude, thereby making it difficult to obtain unambiguous resolution of individual monomers characteristics.

The currently available biological pore membrane system suffers from a number of additional disadvantages, including limited temperature and bias voltage operating ranges, limited chemical environment accommodation, limited device lifetime due to pore diffusion in the membrane, high electronic noise levels associated with large membrane capacitance, and limited availability of pores with the desired diameter and lengths on the 1–10 nm scale. In order to maximize the capabilities of the present technology, certain advances in the technology are required.

SUMMARY OF THE INVENTION

The present invention provides methods and apparatuses based upon solid-state materials for molecular detection. In addition to providing remedies for the above problems associated with biological pores, a solid-state system for molecular detection offers the ability to provide and accommodate local, embedded conducting electrodes and "on chip" integrated electronics that can extend the capabilities of "ionic" current measurements and also offer the prospect of local and very sensitive electronic sensing by mechanisms such as injection tunneling spectroscopy.

In general, the method and apparatus of the invention provide for the traverse of individual monomers of DNA or any other linear polymer molecule across or through a limited volume in space in sequential order, preferably on the nanoscale range, e.g., a volume on a scale which accommodates a single monomer for interacting with a detector such as 1–10,000 nm$^3$, and preferably 1–1000 nm$^3$. The limited space reduces background noise associated with polymer detection, so that subtle differences in structure may be observed. The use of a limited volume also ensures that the monomers move in single file order.

In one aspect of the invention, evaluation of a polymer molecule including linearly connected monomer residues is accomplished by contacting a polymer-containing liquid with an insulating solid-state substrate having a detector capable of detecting polymer molecule characteristics, and causing the polymer molecule to traverse a limited volume on the solid-state substrate so that monomers of the polymer molecule traverse the limited volume in sequential order, whereby the polymer molecule interacts linearly with the detector and data suitable to determine polymer molecule characteristics are obtained.

In another aspect of the invention, evaluation of a polymer molecule including linearly connected monomer residues is accomplished by contacting a polymer-containing liquid with an insulating solid-state membrane having an aperture therein, wherein the aperture includes an entry port and an exit port defining a channel there between, and causing the candidate polymer molecule to traverse the aperture of the membrane, whereby the polymer molecule interacts linearly with the aperture and data suitable to determine polymer molecule characteristics are obtained.

"Solid-state" is used herein to refer to materials that are not of biological origin. By biological origin is meant derived from or isolated from a biological environment such as an organism or cell, or a synthetically manufactured version of a biologically available structure. Solid-state encompasses both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses, although there is no specific limitation to the materials that may be used according to the invention.

A "solid-state substrate" of the invention is an insulating material, which is integratable with the electronic devices, e.g., electrodes, necessary to monitor and detect polymer interactions at the solid-state substrate surface. A solid-state substrate is not required to have an aperture.

A "membrane" is a layer prepared from solid-state materials, in which one or more apertures is formed. The membrane may be a layer, such as a coating or film on a supporting substrate, or it may be a free-standing element. Alternatively, it may be a composite of various materials in a sandwich configuration. The thickness of the membrane may vary, and in particular, the membrane may be considerably thinner in the region containing the aperture. In embodiments, in which the membrane is a layer on a supporting substrate, the supporting substrate includes an appropriately positioned gap, so that the portion of the membrane containing the aperture spans the gap.

An "aperture" of the invention is an opening in a membrane that forms a pore, hole, or channel and is defined by its diameter, length and internal contour. The geometry is not crucial, except for that some constricting asperity may be provided somewhere either at the [rim] periphery or at a point through its length in some embodiments. The walls of the aperture should be electrically insulating; however, it is not required that the entire membrane containing the aperture be insulating, i.e., the membrane in which the aperture exists could be insulating, or the membrane may be conducting, and the aperture walls and membrane may be coated with an insulating material.

"Constraining diameter" is used herein to mean the smallest diameter of the aperture or the channel defined thereby, or an aperture-biomolecule composite. The constraining dimension may arise from an asperity or constriction region within the periphery of the channel. It may be defined by the entirety of the channel if the channel length is sufficiently short. It may be defined by a biomolecule; e.g., a material of "biological origin" as defined herein, which is adjacent to, above, below, or within the membrane aperture. By way of example, see FIGS. 13 and 14. For many embodiments, the length of the constraining diameter feature should be commensurate with the distance between individual monomers of the polymer molecule, e.g., the distance between nucleotides, so that only a single monomer at a time is capable of interacting within the constrained dimension of the aperture. Conducting electrodes may be provided on one or both sides of the membrane to enable detection of species through the aperture when electronic sensing is desired, or to apply a potential to the apparatus. The constraining dimension may also refer to the dimensions of the gap defined by opposing electrode tips or probes, when electrodes are used in an electronic sensing mode.

"Time-dependent" interaction is used herein to mean those types of interactions between the polymer molecule and the detector, e.g., the constraining dimension of the aperture or the electrode tip of the electrodes, and the like, which are time-dependent or monitored as a function of time. For example, the length of a polymer may be related to the time of a single current blockade event. Another time-dependent interaction may be the number of current blockade events per unit time, which is an indication of the number of polymer molecules in solution. Thus, polymer size and polymer concentration also may be considered time-dependent interactions.

"Monomer-dependent" interaction is used herein to mean those types of interactions between the polymer molecule and the detector, e.g., the constraining dimension of the aperture or the electrode tip of the electrodes and the like, which are determined by the nature of the monomer. For example, the chemical composition of individual monomer may be detected as each monomer passes by and interacts at the detector. Thus, polymer monomer identification, e.g., DNA sequencing, is a monomer-dependent interaction.

In preferred embodiments, the channel is coated with an electrically insulating layer or with a passivating layer. The solid-state may be selected from the group consisting of inorganic compounds, organic and inorganic polymers and glasses, and may selected from the group consisting of silicon nitrides, silica, alumina. In preferred embodiments, the solid-state membrane has a thickness in the range of about 10 nm to about 1 mm, and preferably in the range of about 50 nm to about 100 nm. In other embodiments, the solid-state membrane has a capacitance of less than about 0.1 pF.

In other preferred embodiments, the aperture includes a constraining diameter, and the constraining diameter is in the range of less than about 20 nm, preferably less than about 5 nm, and more preferably in the range of about 1–2 nm. The constraining diameter may include a feature integral with the aperture and tapering acutely from a point of constriction in the aperture channel and that taper may be curvilinear, or the taper varies in acuteness along the length of the channel. In some embodiments, the feature is located at the exit or entry port of the aperture, within the channel of the aperture. In other embodiments, the length of the constraining diameter is in the range of 1 to 10 nm, and preferably in the range of 1 to 5 nm.

In other embodiments, the detector comprises first and second electrodes adjacent to the aperture and in electrical communication with the channel. The first and second electrodes are on the same side of the solid-state membrane, or the first and second electrodes are on opposing sides of the solid-state membrane. The electrodes may be a conductive metal layer deposited on the solid-state membrane.

In other embodiments, the detector comprises the constraining diameter of the aperture. In still other embodiments, a polymer replicating catalyst is in contact with the aperture, and the polymer replicating catalyst is located adjacent to, above, below, or within the membrane aperture. The polymer replicating catalyst contains may include a constraining diameter feature.

In other embodiments, the monitoring means includes an ammeter or an electrometer.

In still other embodiments, the means for causing a candidate polymer molecule to traverse the aperture is selected from the group consisting of voltage gradient means and biomotors.

The apparatus may further include at least one insulating layer adjacent to the first and second electrodes, or a substrate supporting the solid-state membrane.

In another aspect of the invention, an apparatus for use in evaluating a linear polymer molecule is described having a first vessel having a first inlet therein, a second vessel having a second inlet therein, and an elongated cylinder having first and second ends, each end in sealing communication with the respective inlets of the first and second vessels. A solid-state membrane containing an electrically insulating aperture therein is disposed in the first end of the elongated cylinder, wherein the aperture includes an entry port and an exit port defining a channel there between, and the membrane is positioned to be contactable with a liquid containing a candidate polymer molecule in the first vessel. Means for causing a candidate polymer molecule to linearly traverse the aperture and a detector for detecting time-dependent or monomer-dependent interactions of a candidate molecule with the aperture are provided.

In another aspect of the invention, a method for evaluating a polymer molecule, the polymer molecule including linearly connected monomer residues includes providing a polymer molecule in a liquid, contacting the liquid with an insulating solid-state substrate having a detector capable of detecting polymer molecule characteristics, causing the polymer molecule to traverse a limited volume on the solid-state substrate so that monomers of the polymer molecule traverse the limit volume in sequential order, whereby the polymer molecule interacts linearly with the detector and data suitable to determine polymer molecule characteristics are obtained.

In some embodiments, the detector is an electrode, and electron current is detected as the monomer traverses the limited volume. The detector is a metal electrode located on the substrate surface, and further includes a polymer replicating catalyst attached to the solid-state surface adjacent to the detector, whereby the polymer replicating catalyst acts upon the polymer molecule, so that the polymer molecule interacts linearly with the detector as it advances through the polymer replicating catalyst. The polymer is selected from the group consisting of polynucleic acids, polynucleotides, DNA and RNA, and the liquid solution further includes reagents necessary to replicate the polymer molecule.

In one embodiment, the limited volume of the solid-state substrate is a groove on the solid-state substrate surface, and the detector is located at the base of the groove, whereby the polymer molecule traverses length of the groove.

In another aspect of the invention, a method for evaluating a polymer molecule including linearly connected monomer residues is provided. A candidate polymer molecule in a liquid is provided and contacted with an insulating solid-state membrane having an aperture therein, wherein the aperture includes an entry port and an exit port defining a channel there between. The candidate polymer molecule traverses the aperture of the membrane, whereby the polymer molecule interacts linearly with the aperture and data suitable to determine polymer molecule characteristics are obtained.

In some embodiments, polymer molecule interactions with the aperture are detected as electronic currents at first and second electrodes adjacent to the aperture and in electrical communication with said channel, or polymer molecule interactions with the aperture are detected by measuring ionic conductance in the channel. Translational current is detected, or current along the length of the channel is detected.

In some embodiments, the polymer molecule traverses the aperture by application of a voltage or use of a biomotor.

In some embodiments, the amplitude of duration of individual conductance measurements is indicative of sequential identity of monomers of the polymer molecule, or the number of changes in the conductance measurement is an indication of the number of monomers in the polymer, the duration of the individual conductance measurement is an indication of the number of monomers in the polymer molecule, or multiple molecules of a heterogeneous mixture of individual polymer molecules are characterized to provide a size distribution of polymers in the mixture.

In other embodiments, a polymer replicating catalyst is in contact with the aperture, and the polymer replicating catalyst is located adjacent to, below, above, or within.

In another aspect of the invention, a method for evaluating a polymer molecule including linearly connected monomer residues includes providing a candidate hybridized polynucleotide molecule in a liquid; and contacting the liquid with an insulating solid-state membrane having an aperture therein, said aperture having a diameter insufficient to permit traversal of the hybridized molecule of the aperture. The candidate polymer molecule traverses the aperture of the membrane, whereby the hybridized polymer molecule is denatured and the single-stranded polymer interacts linearly with the aperture and data suitable to determine polymer molecule characteristics are obtained.

In one embodiment, the hybridized polymer molecule oscillates between a first condition at which the polymer cannot advance into the aperture and a second condition at which the hybridized molecule is denatured and a single strand of the polymer advances into the aperture. The rate of oscillation between the first and second conditions is selected to advance the polymer by about a single monomer with each oscillation. The condition varied is an applied potential gradient across the membrane.

In other embodiments, the rate of traversal of a single strand DNA is an order of magnitude slower when using hybridized polymer than when using a single strand polymer.

The present invention provides a solid-state system for interacting with the polymeric molecule which overcome the limitations of the prior currently available biological pores, such as limited temperature and bias voltage operating ranges, limited chemical environment accommodation, limited device lifetime—due to pore diffusion in the membrane, high electronic noise levels associated with large membrane capacitance, and limited availability of pores with the desired diameter and lengths on the 1–10 nm scale.

BRIEF DESCRIPTION OF THE DRAWING

The invention is described with reference to the figures, which are presented for the purpose of illustration only and are not limiting of the invention, the full scope of which is set forth in the claims which follow.

DESCRIPTION OF THE PREFERRED EMBODIMENTS

Figure 1:
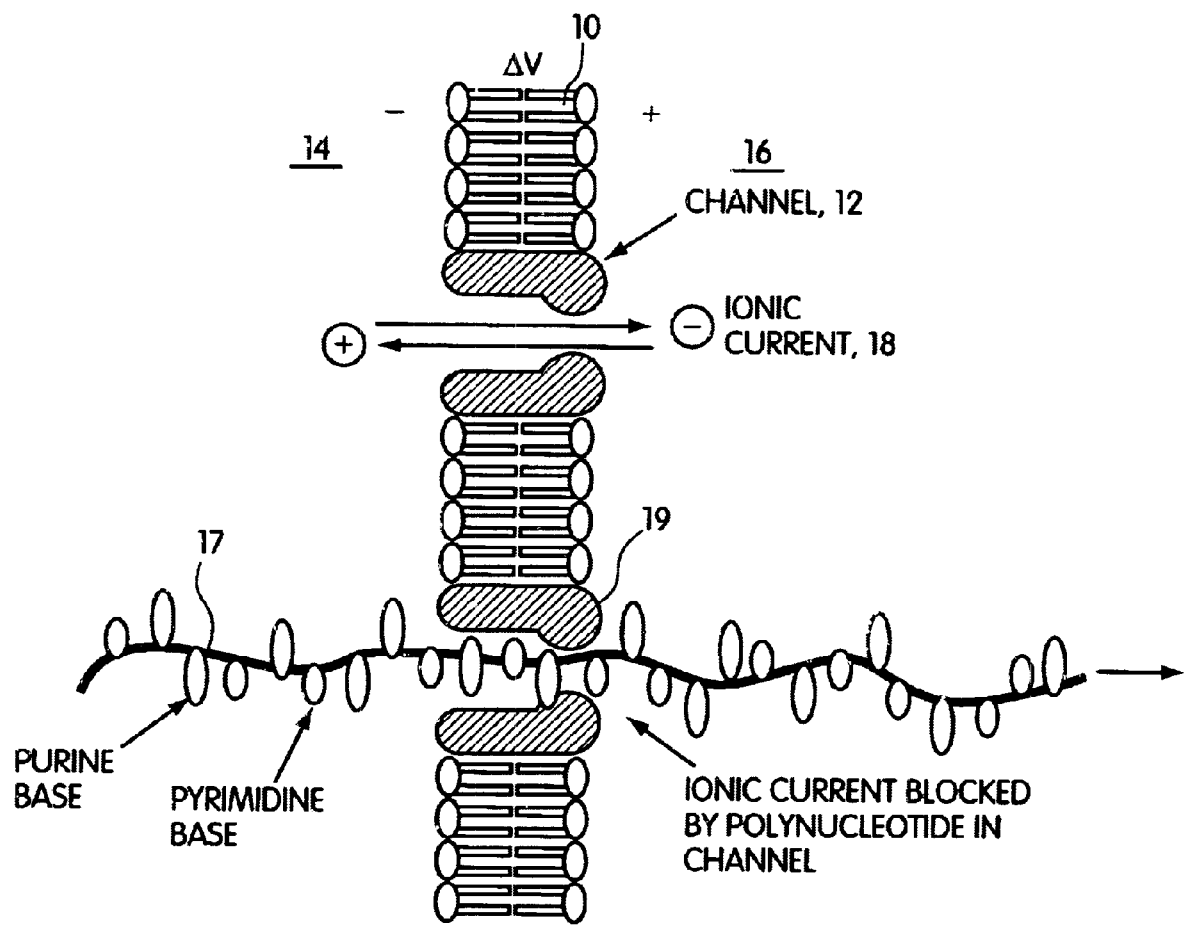
FIG. 1 is an illustration of a prior art protein channel in a lipid bilayer membrane showing translocation of a polymer molecule through the channel.
Figure 2A:
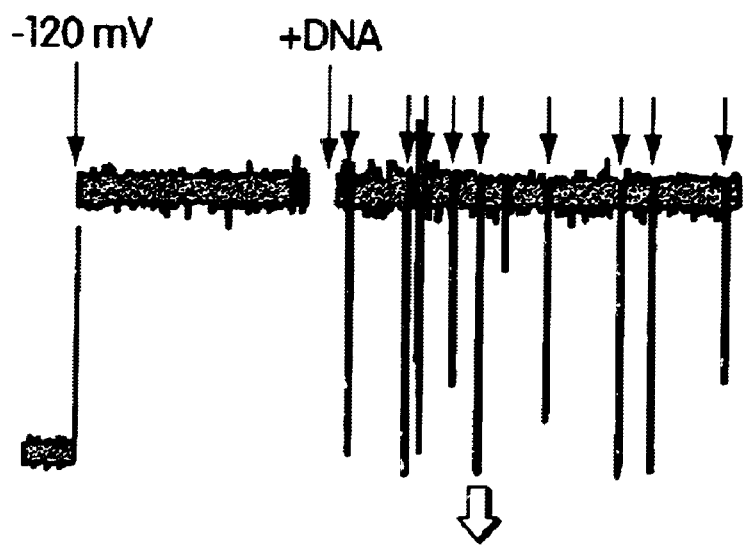
FIG. 2 is a current trace showing the transient drops in ionic current as a DNA molecule is drawn through a *Staphylococcus aureus* α-hemolsin channel in a lipid bilayer.
Figure 2B:
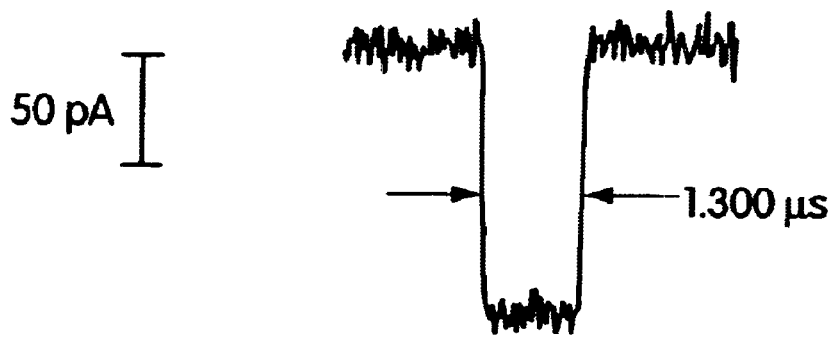

Method and apparatus for evaluation of a polymer molecule are provided that make available monomer-dependent information about the linear polymer molecule. The polymer molecule may be any linear molecule, however, biopolymers such as polynucleic acids, e.g., DNA and RNA and the like, are preferred.

According to one aspect of the invention, an apparatus for evaluation of a polymer molecule includes a solid-state membrane having an aperture therein defining a channel, passageway or opening. The aperture walls are made up of an insulating material. Means for causing the monomers of a candidate polymer molecule to linearly traverse the aperture in single-file order is provided, whereby the polymer molecule interacts with the aperture. A detector is used to identify time-dependent or monomer-dependent interactions of the molecule with the aperture. Additionally, an amplifier or recording mechanism may be used to detect changes in the ionic or electronic conductances across the aperture as the polymer traverses the opening.

At least two modes of detection are contemplated according to the invention. The first type is measures the ionic flow through the channel. For this type of detection, a constraining diameter is the detector. The constraining diameter may be a feature of the aperture, or it may arise from a composite with a molecule of biological origin positioned at, adjacent to, bordering, or within the aperture. In some embodiments, the channel itself may include a constraining diameter that occupies a length of the channel that is commensurate with the distance between monomers and which is of a dimension on the order of the monomer size, so that conductivity is modulated by the molecular interactions of each successive monomer.

The second mode measures electron flow across the aperture diameter or across its length using nanofabricated electrodes suitably placed at the aperture entrance and/or exit. In this embodiment, first and second electrodes adjacent to or bordering the aperture serve as detectors. The electrodes are positioned so as to monitor the candidate polymer molecules that translocate the aperture. Asperities or constraining dimensions defined by the electrode edge or tip provide suitably dimensioned detectors, as they do in scanning tunneling microscopy.

The aperture of the invention is located in a solid-state membrane. The solidstate membrane is chemically inert and/or resistant, and is amenable to processing according to the methods described herein and elsewhere for the fabrication of nanoscale apertures or holes in the substrate. Exemplary materials include, silicon nitride ($Si_3N_4$), alumina ($Al_2O_3$), and silica ($SiO_2$), or plastics such as Teflon® or elastomers such as two-component addition-cure silicone rubber.

The aperture of the invention is of a dimension suitable for interaction with the polymer molecule of interest. Most typically, the interaction will involve translocation of the polymer molecule through the aperture from one side of the substrate to the other; however, it may also include traversal of the polymer across the aperture on one side of the membrane. The aperture may be sized to permit interaction of a single-stranded or double-stranded molecule, i.e., the aperture is of a diameter that is similar to the atomic width of the polymer molecule of interest. In those instances where a single-stranded polynucleotide interacts with the aperture by translocation through the channel, the aperture desirably provides a constraining diameter in the range of about 1–20 nm, and preferably about 1–10 nm, and more preferably in the range of about 1–2 nm. In those instances where a double-stranded polynucleotide translocates across the channel, the aperture desirably provides a constraining diameter in the range of about 2–20 nm, and preferably in the range of about 2–10 nm, and more preferably in the range of 2–4 nm. The aperture need not be of this diameter throughout the entirety of its length, so long as a constriction or narrowing along its length of the appropriate dimension exists. Furthermore, and particularly when using the second, electron flow mode of measurement, the constraining diameter feature may be defined by the electrode edges or tips.

In order to sense changes in the ionic or electronic conductance of the channel, the walls of the aperture are insulating. In one embodiment of the invention, the membrane is an insulating material and the aperture is formed therein, and no further fabrication steps are necessary. In other embodiments, the membrane may be conducting; in which case, the walls of the aperture may be coated with an insulating layer. By way of example, an aperture first may be made in the membrane having a diameter larger than the desired final dimension. An insulating layer is then deposited on the walls of the aperture that is suitable to provide the desired insulating properties and the desired final channel diameter dimensions. Insulating layers may be formed using conventional chemical and physical thin layer deposition techniques, or they may be obtained by first preparing a composite material substrate containing insulating domains in the conductive matrix of the substrate, and forming apertures in the insulating domains of the composite substrate.

In other embodiments, the walls of the channel may be coated to passivate the surface or otherwise modify the electrical properties of the aperture. For example, a single atomic layer of an organic or inorganic material may be deposited to reduce atomic-scale irregularities of the surface, resulting from the etching techniques used in fabrication of the aperture. The coating may be a biomolecule such as a protein. Furthermore, the contour, size and shape of the aperture are selected to allow accurate current measurements and otherwise improve the quality of the gathered data. The preferred aperture features may vary dependent upon whether ionic or electronic sensing is being used and depending upon whether a high degree of resolution is desired or needed. The aperture features will also vary dependent upon whether the aperture defines the constraining diameter feature, or is intended to accommodate a molecule of biological origin, or a coating within the aperture.

When sensing is accomplished by measuring changes in the ionic current of the aperture, the aperture preferably provides a constraining diameter on the order of the atomic width of the molecule, which in the case of DNA is about 1–2 nm. Where high resolution, e.g., information regarding individual monomers, is desired, the aperture presents an inwardly projecting, very thin edge or asperity to the polymer molecule so that a narrow, well-defined contact, or near contact, between the polymer and the detector is made. The length of that contact, e.g., the length of the constraining diameter feature, may range from about $\leq 0.1$ to 10 nm, and preferably is no more than about 5 nm, and more preferably no greater than a single monomer residue, which in the case of DNA is about 0.3–0.4 nm. In other embodiments, high resolution may not be required, for example, where the translocation time of the polymer through the aperture is being measured. In those instances, the length of the constraining diameter feature is not of critical importance and may vary, for example, in the range of about 1 to 100 nm. The total length of the channel (not just the constraining diameter) is not of critical importance to the method and apparatus; however, it is desirable that the aperture channel dimensions approaching the constraining diameter be sufficiently large so as not to reduce ionic flow through the channel or to form a well-defined polymer-aperture contact separate from that in the constraining diameter portion of the channel.

When sensing is accomplished by measuring changes in the electron current employing the techniques of electron tunneling microscopy, no specific constraints are placed upon the aperture geometry other than that it be adequate to permit only a single polymer molecule at a time to traverse the aperture, and that the molecule travel in an extended conformation, e.g., without secondary structure. Detection is carried out at the electron tip, which provides the required interaction and detection of the polymer.

Various aperture geometries are shown in FIG. 3. In preferred embodiments, the constraining diameter feature 30 is integral with the aperture and tapers away rapidly from a point of constriction 32, for example at an acute angle (less than or equal to about 45°), until it joins the channel wall 34 at its widened base 36. The feature is not required to taper angularly from the point of constriction, as shown in FIG. 3A, but may also have curvilinear features as shown in FIG. 3B. Alternatively, the aperture may possess step-like channel walls, so that the constraining diameter feature tapers sharply at the point of constriction, and then more gently as the aperture approaches the opposite substrate face, as is shown in FIG. 3C. Lastly, it is understood that the constraining diameter feature may be located at any place throughout the length of the channel and need not be at the intersection between the channel length and the membrane surface. These alternative positions for the constraining diameter are shown in FIGS. 3D–E.

When sensing is accomplished by electron tunneling, there is no particular length requirement of the aperture. In other embodiments relating to ionic current measurement, where either or both the duration of translocation or the ionic current during translocation is the variable of interest, it may be desirable that the length of the channel be shorter than the polymer molecule. When the polymer molecule is shorter than the channel, the time it takes for the polymer to get through the aperture is determined by the length of the channel and not the length of the polymer molecule. Exemplary channel lengths (based on total membrane thickness) may be in the range of $\leq 0.1$–1000 nm, or greater.

In yet other embodiments, the channel length is sufficient to minimize variations in the time of polymer aperture translocation due to entropic variations among polymer molecules. A polymer molecule in solution has more degrees of freedom than a polymer molecule constrained within the aperture channel. Furthermore, entropy varies among polymer molecules of the same composition, depending upon their local solution environments. When the polymer enters the aperture, its movement is constrained and entropy is lost. This loss of entropy represents a barrier to entry into the aperture, which varies in magnitude based on initial entropic condition of the molecule. Therefore, the time of entry into the aperture will vary even among polymers having the same composition. By extending the length of the channel so that the entropic effects on entry into the constriction where measurement takes place are minimized, it is expected that variations of residence time in the measurement constriction region will be minimized.

In one non-limiting embodiment, the membrane is relatively thick (50–100 nm) and tapers to form a constraining aperture diameter of 1.5 to 1.8 nm. The length at the constraining diameter is short (about 0.1–1 nm).

When drawn through the channel by an approximately 100 mV bias, single-stranded polynucleotides traverse the channel at rates approaching 1 nucleotide/$\mu$s. Precise current measurements at this very high bandwidth require a much thicker, lower capacitance membrane than is possible to obtain using a lipid bilayer ($\approx$5 nm thick). Capacitance is inversely proportionate to thickness and directly proportional to surface area, so that membranes that are thick over most of their surface area are preferred. As is apparent to one of ordinary skill in the art, the membrane in which the aperture is formed may be many times thicker than a lipid bilayer. The solid-state membranes of the invention may be fabricated with virtually any desired thickness and with any desired aspect ratio (profile when viewed from the side), when prepared according to the methods described herein. In fact, the membrane may be any thickness, by way of example only, on the order of 10 nm to 1 mm, and preferably in the range of 50 nm to 0.1 µm, although there may be reasons to limit the thickness of the membrane at the aperture, e.g., the length of the constraining diameter so as to provide a channel having the appropriate constraining dimension for certain experimental conditions. Although the solid-state membrane may be quite thin at its constraining diameter feature, the overall membrane thickness is very large, thereby keeping the overall low capacitance of the system low. Thus, a membrane and aperture system of sufficient thickness to attain a low capacitance system is prepared, and the mechanical and chemical robustness of the membrane is provided in combination with low capacitance for high bandwidth, high-resolution evaluation of biopolymers.

When considering the capacitance of the membrane/aperture system, the entire structure of the system is considered. For both ionic and electronic methods, the capacitance is desirably low, but the structures that contribute to the capacitance at issue may differ in ionic and electronic methods. For example, when a voltage gradient is applied across the membrane (either ionic or electronic method, the latter with electrically conductive surfaces on both sides of the substrate), the thickness of the membrane is important. However, when a voltage gradient is applied transversely across the aperture, the space between the edges of the two electrodes on the same surface is a potential source of capacitance. Therefore, the length of the edges of the two electrodes where they approach the aperture should be short (as shown in FIG. 7B, below).

In preferred embodiments, the solid-state membrane containing the aperture is provided with a conductive, i.e., metallic, layer or thin film that serves as an electrode. The conductive regions are in close proximity to the aperture for high local sensitivity to conductance or electronic variations in both the transverse (along the channel) or longitudinal (across the channel opening) directions. The electrodes may be used in conjunction with either ionic or electronic sensing, as is described herein. Aside from ionic and electronic sensing, it is within the scope of the invention to exploit the mechanical, optical, induced charging or other properties of the polymer molecule/aperture system to obtain the desired sequential record of the molecular structure as it passes through or past the aperture.

Microfabrication of an Aperture in a Solid-state Membrane

A method is provided to prepare a membrane having an aperture of the size and geometry required by the invention. Further details are provided in co-pending application filed on even date herewith and entitled "Control of Solid State Dimensional Features," which is incorporated by reference.

The microfabrication method generally involves forming a cavity (not a hole) in the membrane. The geometry of the cavity is not of critical importance. The membrane surface is progressively thinned from the cavity free surface (or the cavity surface) of the substrate until it intersects with the cavity to form an aperture. The extent of further thinning beyond this point determines the size of the aperture.

Figure 4A:
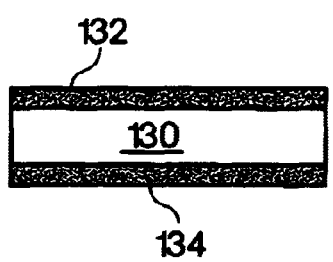
FIGS. 4 A–G illustrate the step-by-step fabrication of the aperture/membrane system of the invention.

Referring to FIG. 4, in an example microfabrication process provided by the invention for forming an aperture in a membrane, a starting substrate 130, e.g., a silicon wafer, is provided, as shown in FIG. 4A. A selected membrane material, e.g., silicon nitride, is provided as coating layers 132, 134 on the upper and lower surfaces, respectively, of the wafer. The thickness of the coating layer 134 is that thickness selected for the solid-state substrate to be formed.

In one example, a silicon-rich, low-stress, silicon nitride layer of about 50 nm in thickness is deposited on the silicon wafer by conventional chemical vapor deposition (CVD) processing. Silicon nitride has several particular advantages for the application of the invention. For example, silicon nitride is characterized by very high dielectric breakdown strength of about $10^7$ volts per meter, and a very high dc resistivity of $10^{14}$ ohm-cm. In addition, silicon nitride is mechanically very strong and stable at high temperatures, and is relatively impervious to a wide range of chemical environments. Importantly, the surface of silicon nitride is readily wetted by water, thereby minimizing the formation of air bubbles in the aperture when in contact with a liquid solution, e.g., a DNA solution.

It is recognized that additional membrane materials, e.g., silicon dioxide, can be deposited before or after deposition of the silicon nitride layers for mechanical stress control or other consideration. The silicon nitride layer can also be further processed, e.g., by ion implantation, to control mechanical membrane stress or adjust electrical or thermal conductivity of the membrane as desired for a given application.

Figure 4B:
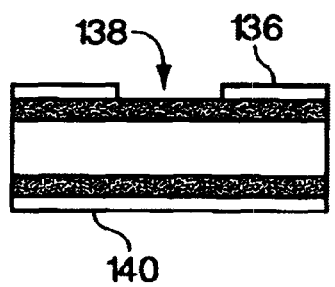
Figure 4C:
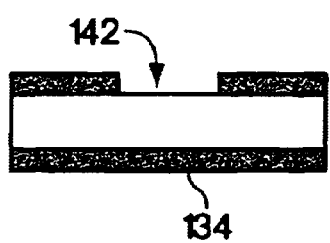

As shown in FIG. 4B, a layer of photoresist 136 is formed on one of the deposited nitride layers and patterned to define a nitride etch window 138. The opposing surface of the wafer is blanket coated with a photoresist layer 140. Then, as shown in FIG. 4C, the silicon nitride exposed by the nitride etch window 138 is removed by, e.g., conventional reactive ion etching techniques. This exposes a substrate etch window 142. The opposing nitride layer 134 is protected from this etch by the blanket photoresist layer 140, which is removed at the etch completion.

Figure 4D:
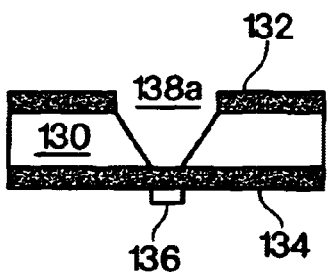

Next, referring to FIG. 4D, the silicon wafer is bulk micromachined by a suitable etch procedure, e.g., a conventional anisotropic wet etch process employing KOH. Preferably, the bulk wafer etch process employed is characterized by a high selectivity to the wafer material over the membrane material. In the example illustrated, the KOH etch substantially does not attack the silicon nitride layers. Continuation of the etch through the thickness of the wafer thereby produces a self-supporting nitride membrane region 136 in a nitride layer 134. The nitride membrane forms the bottom of a pyramidal well 138a etched out of the silicon wafer due to the anisotropic, crystallographic-specific nature of the KOH etch. The span of the nitride membrane region is thus determined by the thickness and crystallographic orientation of the starting silicon wafer. As will be recognized, the membrane dimensions can therefore be controlled as desired. As will further be recognized, a wide range of alternative wet- and dry-etch processes can be employed to remove the silicon substrate in the desired membrane region.

Figure 4E:
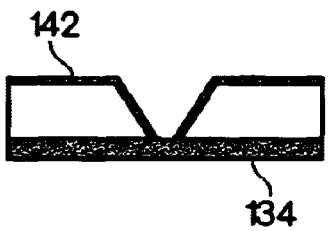

Referring to FIG. 4E, the remaining layer 132 of silicon nitride opposite the membrane layer can then removed if desired by, e.g., conventional reactive ion etching, and then a layer of silicon dioxide 142 is optionally grown on the exposed silicon surfaces if electrical insulation of the silicon wafer is desired for a given application. Conventional wet or thermal oxide growth can be preferred over a CVD oxide layer such that oxide is only formed on the silicon surfaces in the manner illustrated. If, however, a composite membrane is desired, e.g., for mechanical stress control, then a CVD or other deposition process can be employed to produce an oxide layer on both the silicon wafer and the lower silicon nitride membrane surfaces, or on the nitride membrane surface alone.

Figure 4F:
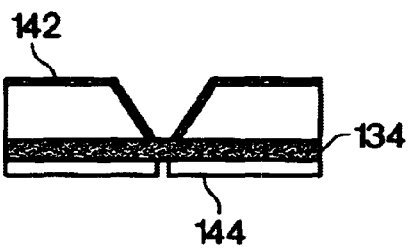
Figure 4G:
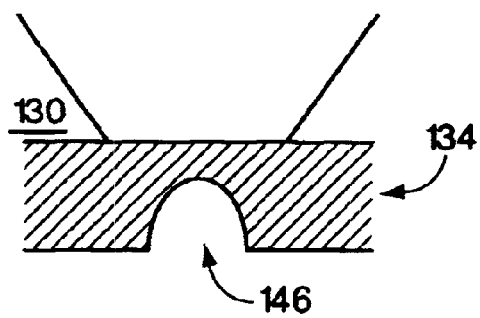

In a next step of the process, referring to FIGS. 4F–4G, a cavity 146 is etched in a selected surface of the membrane 136. In one example process, as illustrated, a layer of resist 144 is formed on the lower membrane surface, i.e., the membrane surface opposite that in the pyramidal wafer well 138a. The resist is then lithographically patterned to define the cavity to be formed in the membrane. This pattern can be, for example, e-beam lithography or photolithography as prescribed for the cavity dimensions to be produced. The choice of surface for the cavity is preferably selected to enable lithography on a flat surface. It can be difficult to effectively pattern a layer of resist provided on the membrane surface at the bottom of the silicon pyramidal well. If desired for a given application, however, the cavity can be formed on such a surface with lithographic techniques specific to such a configuration.

Figure 3A:
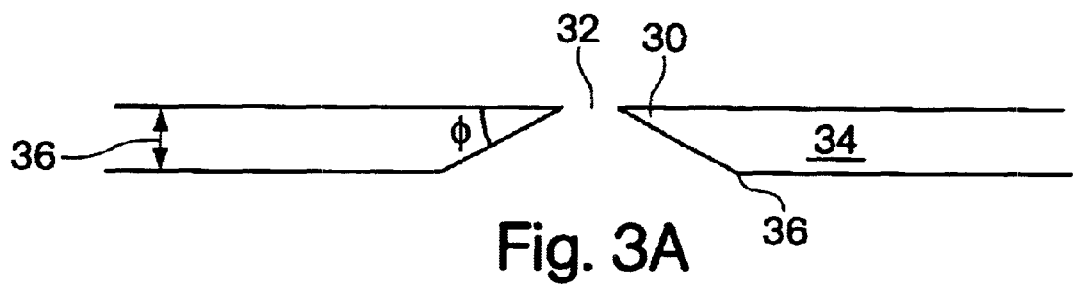
FIGS. 3 A–E are cross-sectional illustrations of aperture geometries of the present invention for measuring variations in ionic current.
Figure 3B:
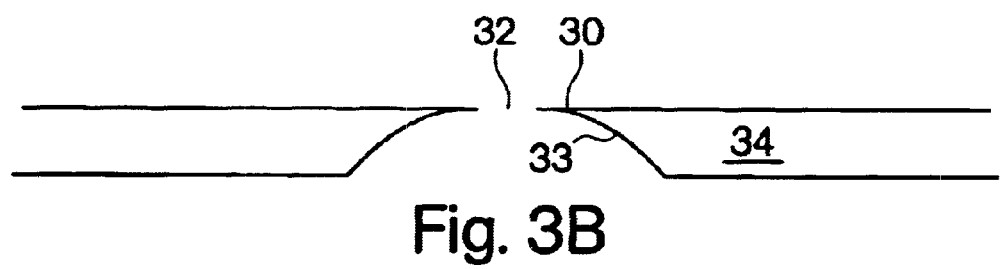
Figure 3C:
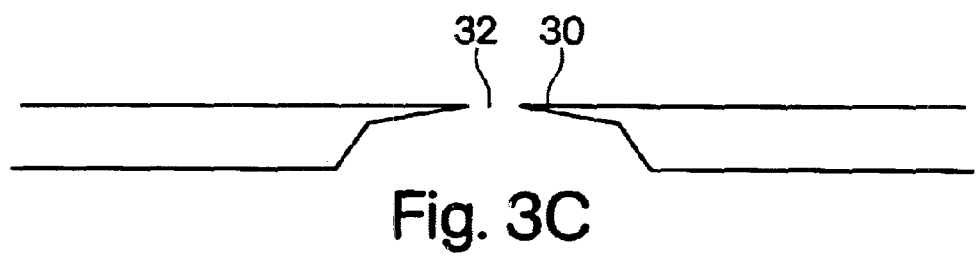
Figure 3D:
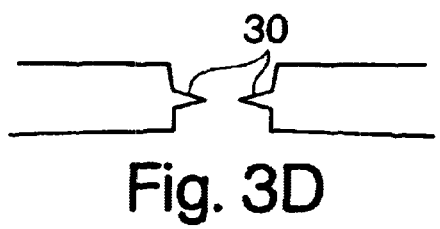
Figure 3E:
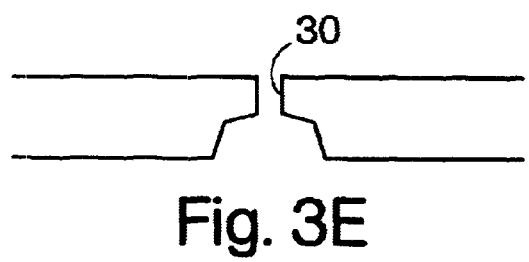

The sidewall profile of the cavity to be formed in the membrane can be specified to produce a selected aperture geometry, e.g., those profiles shown in FIGS. 3A–3E. The lithographic step defining the cavity, as well as the nature of the cavity etch process itself, can also be employed to define the cavity sidewall profile. In one example scenario, the selected lithographic cavity pattern is continuous, e.g., as a circle, and a relatively isotropic etch process, e.g., a reactive ion etch process, is carried out to form a bowl-shaped cavity 33 in the nitride membrane 34, as shown in FIG. 3B. The isotropic nature of the nitride reactive ion etch process inherently forms the bowl shape extending from a circular lithographic pattern.

Substantially any lithographic cavity pattern may be used for achieving a desired cavity geometry. Square, rectangle, hexagonal, or other pattern, symmetric or asymmetric, can be employed. Due to the batch nature of the lithographic and other microfabrication processes employed in the aperture forming method, arrays of cavities, of varying extent and geometry, can be defined in a single structure such as the membrane illustrated. Because the aperture formation process of the invention relies on structural thinning, rather than lithography, to define the final aperture geometry, the largest lateral dimension of the cavity can be much greater than the final constraining aperture diameter; in general, the largest cavity pattern dimension can be one or more orders of magnitude larger than a selected constraining aperture diameter. The cavity thins inward from the membrane surface to terminate at an interior point in the membrane. We refer to the termination point of the cavity as the cavity bottom. Preferably, given the characteristics of a selected cavity etch process, the cavity pattern extent is correspondingly selected to produce a desired extent at the cavity bottom, and to produce a range of cavity expanses between the cavity bottom and the membrane surface. Further details are found in United States application entitled "Control of Solid State Dimensional Features," filed on even date herewith, incorporated herein by reference.

Once cavity 146 has been formed in the membrane, thinning of the membrane is then carried out on either side of the membrane 134. Typically thinning occurs on the surface opposite that of the cavity by an appropriate procedure to open the aperture, e.g., the membrane surface in the pyramidal wafer well. Thus, it is apparent that the location of the constraining diameter may be located at any point along the length of the aperture channel, by selection of the depth of the cavity 146 prior to thinning of the membrane from the opposing side.

A wide range of thinning processes may be used; all that is required is the ability to etch back the membrane from either face. For many applications, a particularly well-suited thinning process is ion beam sputtering. In such a process, a beam of ions is directed to the membrane surface to be thinned to sputter etch away material from that surface. In typical ion beam sputtering processes, for every incident ion, on average, a single atom of material is ejected from the sputtering target; sputtering may thus be considered as an atomic-scale version of "sand blasting." In the case of, e.g., a silicon nitride membrane, such sputter etching results in the removal of about one atomic layer of silicon nitride from the membrane per second. When the surface exposed to the sputtering beam has been sufficiently thinned that the surface intersects with the cavity bottom, an aperture is formed.

Additional thinning processes include ion beam assisted etching, electron beam etching or assisted etching, plasma and reactive ion etching, wet etching such as electrochemical etching, chemomechanical polishing, and other fabrication and manufacturing processes that enable controlled thinning of a structure to intersect a cavity on a surface opposite that being thinned. See, United States application entitled "Control of Solid State Dimensional Features," filed on even date herewith, incorporated by reference, for further details. Whatever aperture formation process is selected, highly precise aperture formation can be accomplished by implementing a feedback mechanism during the thinning process. This feedback mechanism is based on detection of a physical species provided during the thinning etch in a manner that is indicative of the physical dimensions of a feature, e.g., an aperture, that is being produced by the etch. Such feedback enables real time control of the aperture formation process, whereby a precise and prespecified aperture diameter can be reliably and reproducibly formed. See, United States application entitled "Control of Solid State Dimensional Features, " filed on even date herewith, incorporated by reference, for further detail.

The invention does not require that the aperture formation process employ feedback, but if such does, both subtractive and additive processes can be controlled by the feedback techniques of the invention. For example, an aperture a given dimension can be diminished by a suitable process, during which the physical species detection and feedback process control of the invention is imposed to control the diminishing process.

Additive processes such as sintering, heating, material deposition, material growth, and other suitable processes are contemplated as being controllable by the feedback mechanism of the invention. A particularly well-suited additive processes employs ion beam irradiation of the membrane under appropriate membrane temperature and ion beam energy and flux conditions to cause material flow and transport to the aperture rim, whereby the aperture mouth extent is controllably diminished. In conjunction with the feedback mechanism of the invention, this enables precise formation of an aperture based on a relatively macro-scale starting aperture. Similarly, oxidation, swelling, condensation, evaporation, electroplating, ion- or electron-assisted deposition or growth, and other such additive processes can be controlled in accordance with the invention. See, United States application entitled "Control of Solid State Dimensional Features," filed on even date herewith and incorporated by reference, for further detail.

It is to be recognized that in accordance with the invention, the membrane aperture can be formed in conjunction with, or after, the formation of electrically conductive and dielectric layers in the region of the membrane. It is not strictly required that the aperture be formed prior to deposition and patterning of layers required for a given application.

Detector Apparatus

Figure 5A:
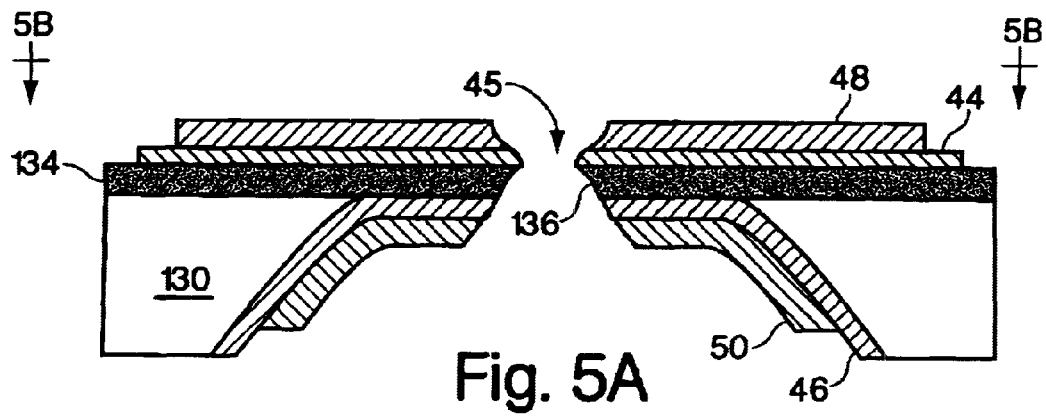
FIG. 5 is (A) a side view and (B) a plan view of one embodiment of a composite solid-state membrane of the invention.
Figure 5B:
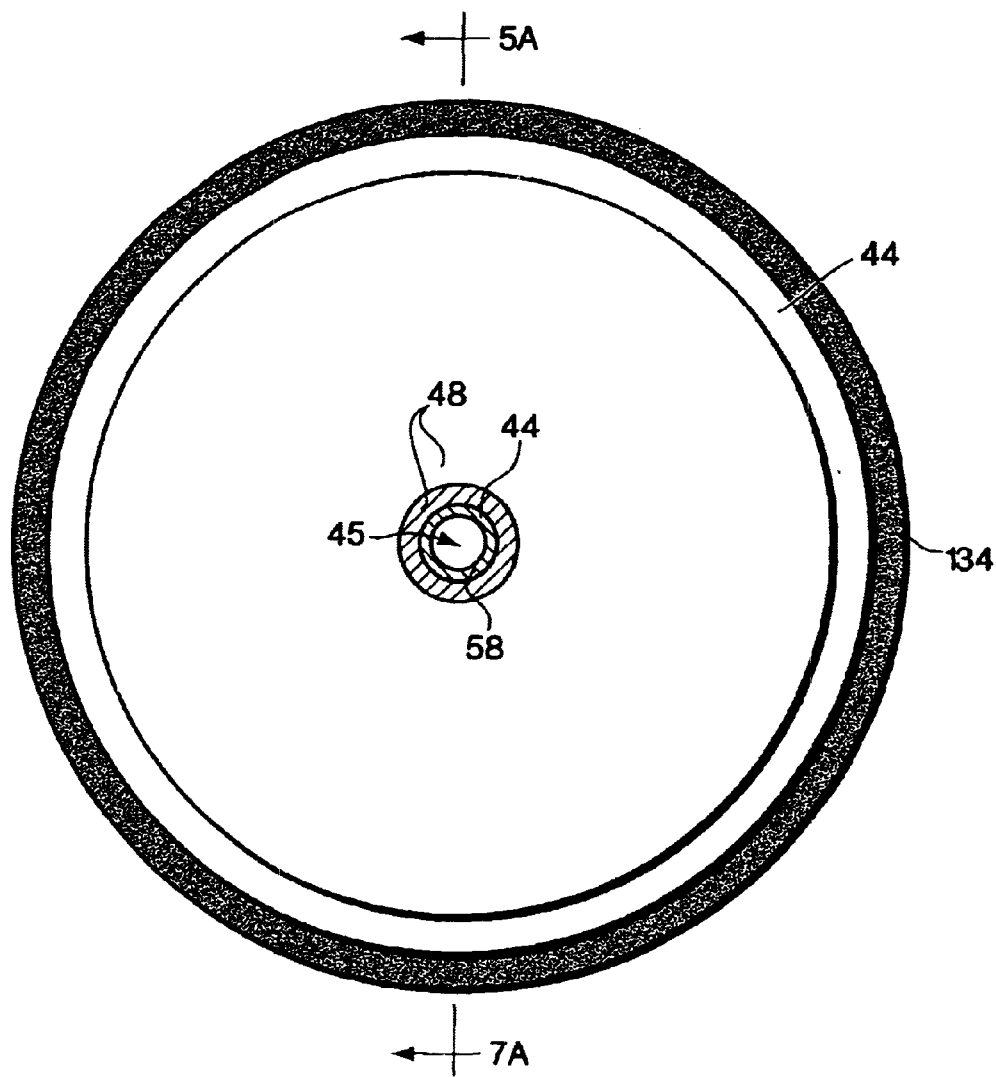

Once a solid-state membrane having an aperture of appropriate dimensions is provided, one or more electrical contacts are formed on the membrane in a configuration suitable for a selected detection and/or sequencing mechanism. For example, where a longitudinal electron tunneling detection mechanism is to be employed, both sides of the membrane can be metallized to provide tunneling electrodes at each longitudinal end of the aperture. Referring to FIGS. 5A–B in which features shown in FIGS. 4A–G are similarly labeled, in this configuration electrically conductive layers 44, 46 are provided on opposite surfaces of the membrane 136 in the region adjacent to the aperture opening 45. The invention contemplates a range of processes for producing the conductive layers. For example, conventional sputter deposition of a metal, e.g., chrome, silver, gold, palladium, or other metal, can be carried out. Electroplating can also be employed.

Figure 6:
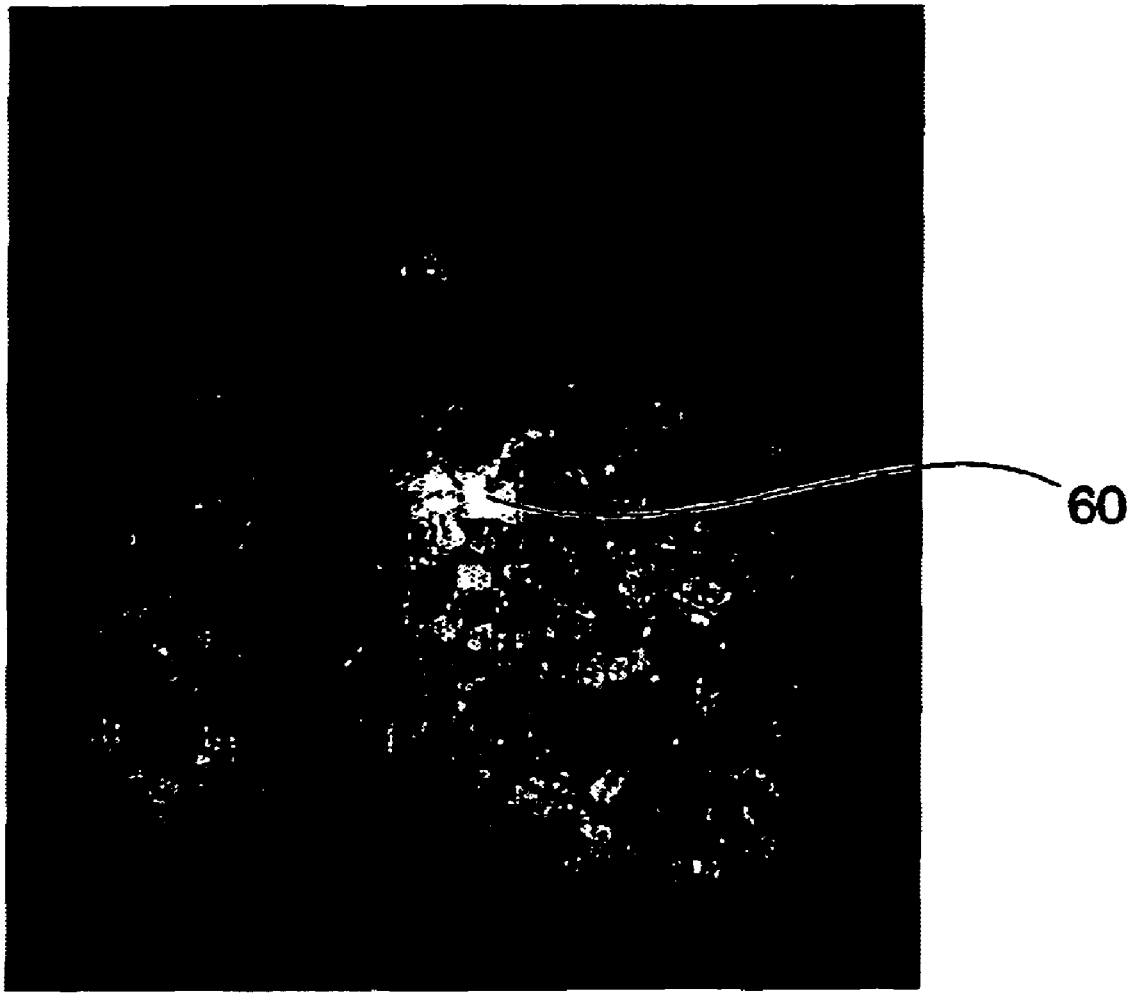
FIG. 6 is a photomicrograph of a metallized aperture.

Referring also to FIG. 6, there is shown an electron micrograph of a 500 nm thick silicon nitride layer in which an aperture has been formed a focused ion beam. The layer includes an aperture 60 having a diameter of 10 nm, obtained by subsequent sputtering to decrease the pore size made by ion beams, and on which has been sputter deposited a chrome layer (4 nm chromium and 15 nm silver). The resulting metal film completely covers the silicon nitride surface without filling the aperture. As indicated in the image, the aperture remained open during the sputtering process, although the chromium metal has crystallized, and sharp edges of the crystal intrude into the hole so that its circumference is partially obscured. It is therefore contemplated in accordance with the invention that a membrane including an aperture can be coated with a metal layer while the aperture dimensions are substantially preserved.

Referring back to FIGS. 5A–B, for many applications, it may be preferred that the electrically conductive layers 44, 46 be substantially electrically isolated from the solution in which the membrane is maintained during a sequencing operation. To this end, dielectric layers 48, 50 can be deposited on the conductive layers 44, 46, respectively. In one example process, a layer of silicon dioxide or silicon nitride is deposited on each conductive layer and then photolithographically patterned and etched by, e.g., reactive ion etching, focused ion beam etching, or plasma etching to remove the dielectric from the aperture and the area immediately surrounding it. Preferably, the dielectric layer is also removed at its periphery to expose a region of the electrically conductive layers for making electrical contact with those layers.

Figure 7A:
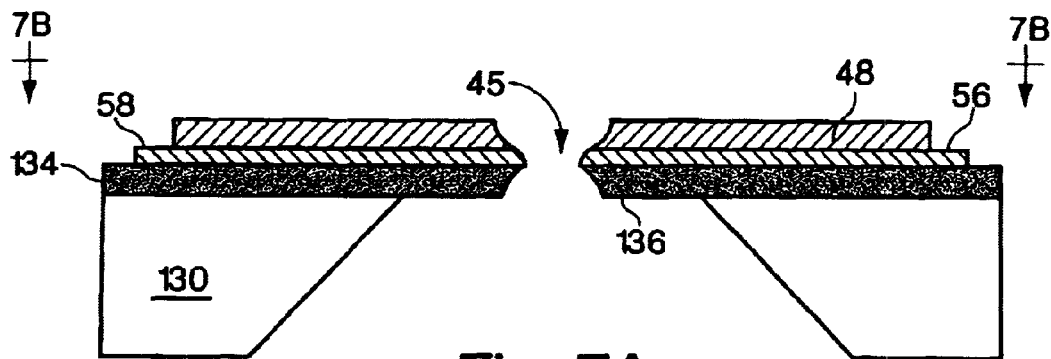
FIG. 7 is (A) a side view and (B) a plan view of another embodiment of the solid-state membrane of the invention.
Figure 7B:
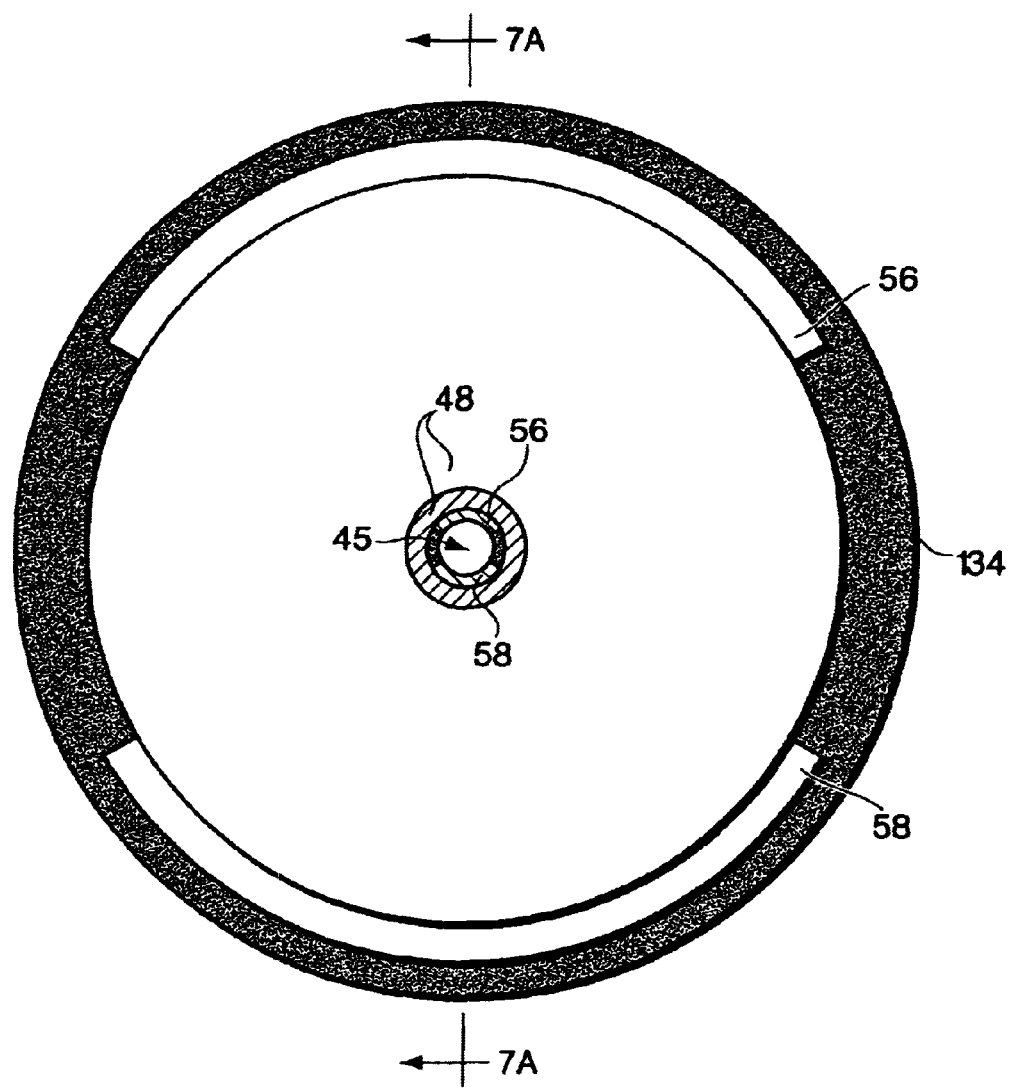

Referring to FIGS. 7A–B, there is shown a device configuration including electrically conductive layers for enabling sequencing and detection by transverse electron tunneling. In this configuration, a conductive layer 44 is provided on one side of the membrane 36 in the region of the aperture opening 45. As shown in FIG. 7B, the conductive layer 44 is divided into two or more electrically isolated conducting regions 56, 58. This enables electron-tunneling detection transversely across the aperture opening as a molecule passes through the aperture, in the manner described above. The electrically-isolated conducting regions 56, 58 may be formed by any suitable process, e.g., focused ion beam etching of a continuous layer, direct-write electron or focused ion beam deposition, ion assisted deposition, or other process that enables the formation of electrically-isolated conducting regions. If desirable for a given application, a dielectric material 48 can be provided on the conducting layer 44 to isolate the conducting layer 44 from the solution in which the membrane is operating.

In operation, a liquid containing a polymer molecule of interest may be placed in contact with the cis side of the membrane. A receiving liquid typically is located on the trans side of the membrane. In preferred embodiments, the liquid is a weakly electrically conductive medium, which can be the same or different on the cis-trans sides of the substrate. A negatively biased potential gradient may be applied across the two liquids, or across the first and second electrodes adjacent to the solid-state membrane, such that ionic currents flow between the negatively biased side of the apparatus to the positive side. Other ways of inducing polymer transport through the aperture is by using a biological motor, as discussed herein. These motors will pick up polymer molecules and transport the molecules in single file order through a defined and limited area of space to which a suitable detector can be coupled.

Figure 8A:
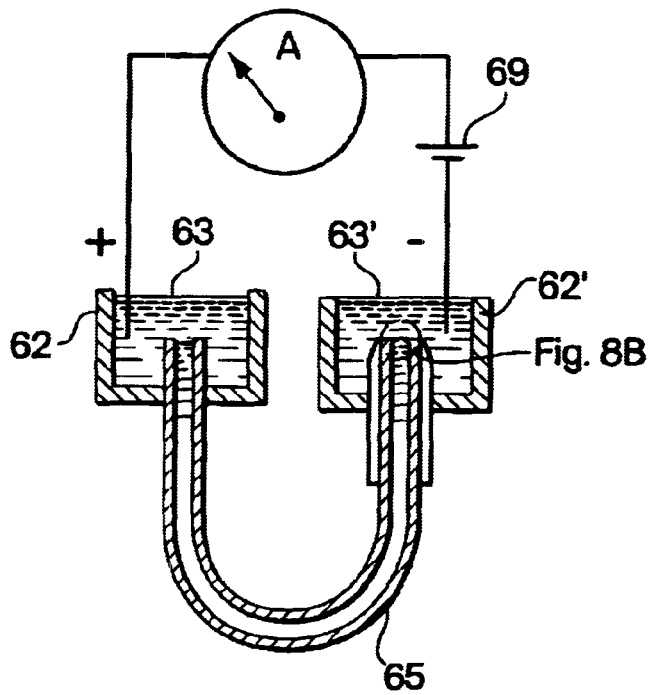
FIGS. 8 A–B are side views of another embodiment of the apparatus of the invention, based upon a modified patch-clamp apparatus.
Figure 8B:
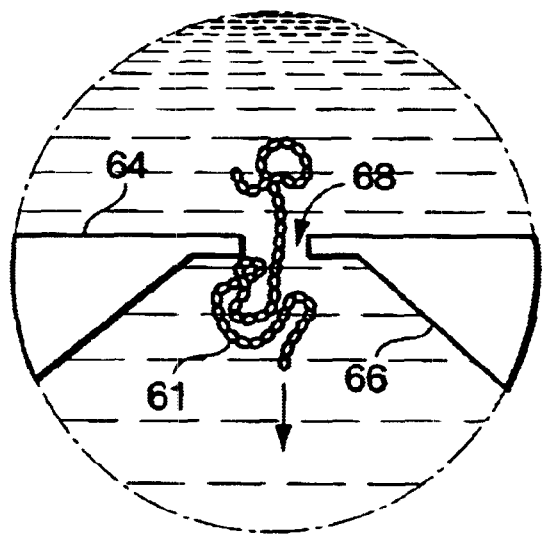

In operation, an apparatus such as shown in FIGS. 8A–8B may be used. A U-shaped patch tube 65 connects two fluid-filled baths 62, 62' containing electrically conducting liquids 63, 63'. The polymer molecule 61 to be investigated is contained in a liquid 63' in bath 62'(cis side of the substrate). One end 64 of the patch tube has a solid-state substrate 66 that narrows to form an aperture 68 (shown in inset, FIG. 8B), which is located in liquid 63'. The electrically conductive liquids are in electrical connection with electrodes, e.g., silver/silver chloride electrodes, and a power source 69 for establishing a voltage gradient across the aperture. In operation, a voltage gradient, e.g., −120 mV, is applied and polymer molecules are driven through the aperture 68 and into the trans side of the membrane. Changes to ionic conductance associated by molecular translocation are detected by a sensitive ammeter.

The U-tube device has proved to exhibit low noise and high levels of convenience and is a preferred set-up for evaluating solid-state membrane devices. The apparatus requires a very small volume of liquid (50 µL for both chambers and the connecting tube), provides easy access an view of the solid-state substrate which lies in a horizontal plane, exhibits very low noise (around 0.3 pA rms at 5 kHz), and can be fabricated using two simple stainless steel molds and heat-shrinkable Teflon® tubing. The entire apparatus may be viewed under a microscope so that the membrane is easily observed.

Figure 9A:
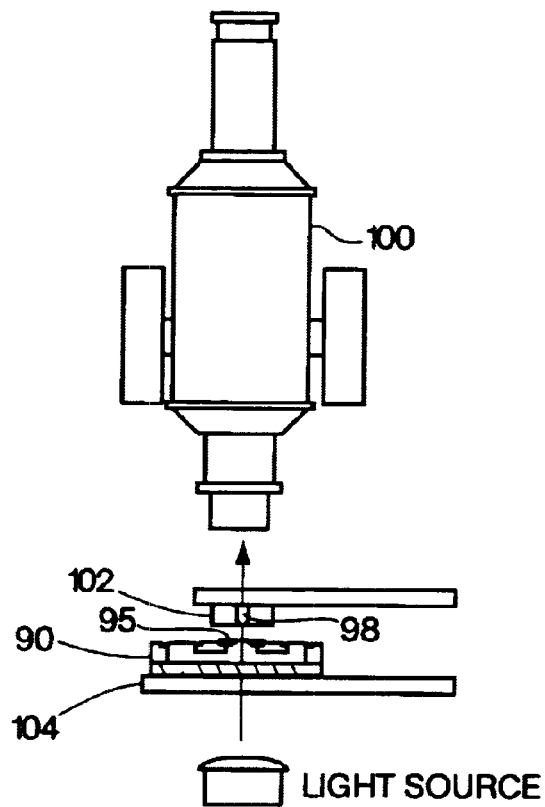
FIGS. 9 A–B are (A) pictorial and (B) cross-sectional illustrations of an apparatus of the invention.
Figure 9B:
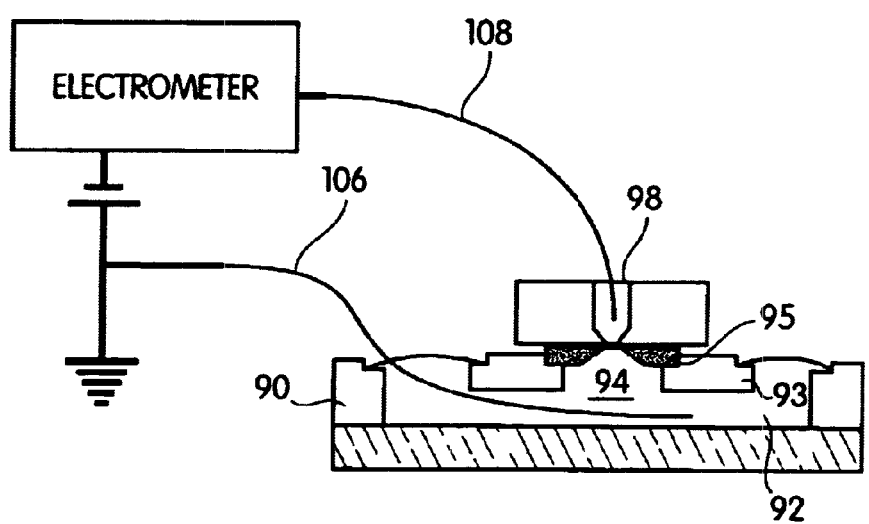

FIGS. 9A–9B illustrate an apparatus that incorporates the membrane and aperture into a device equipped with liquid-holding vessels for evaluation of polymers in solution. A container 90 houses an electrically conducting solution 92. A sample holder 93, e.g., a silicone rubber (PDMS) sample holder, is positioned in the container 90, contacting the solution and forming a fluid-filled channel 94. A solid-state membrane 95 containing the nanoscale aperture is positioned in the sample holder. In operation, the substrate contacts the fluid channel 94. A funnel 98, e.g., a silicone rubber (PDMS) funnel, is positioned above the aperture of the window created by silicon support to which the substrate solid-state membrane is adhered. The funnel has an aperture dimension similar to, or only slightly greater than, the dimension of the free-standing portion of the solid-state membrane, e.g., about 40 µm, which minimizes background noise. Alignment of the funnel aperture with that of the solidstate membrane is accomplished using an alignment microscope 100 and 3-axis manipulators 102, 104. Once aligned, a seal is formed between the silicon nitride and silicone rubber surfaces, for example, by pressure application. An electrically conducting polymer solution is introduced into the funnel. An electrochemical cell is established between the two ionic solutions using electrodes 106, 108, e.g., silver chloride electrodes, separated by the silicon nitride membrane. A potential gradient is applied between the two electrodes and ionic current is monitored to detect changes in the ionic current of the electrochemical cell.

Once such an ionic flow is established, its diminution due to blockages of the channel by translocating molecules may be measured using an ammeter capable of measuring very small current (pA to nA) levels. In other embodiments, the electronic current due to tunneling effects (discussed in greater detail herein below) may be monitored.

The characteristics of the polymer can be identified by the noise level, amplitude or duration, other properties of the signal, or of the individual conductance changes. Such changes can identify the monomers in sequence, as each monomer will have a characteristic conductance change signature. For instance, the volume, shape or charge on each monomer will affect conductance in a characteristic way. Likewise, the size of the entire polymer can be determined by observing the length of the time (duration) that monomer-dependent conductance changes occur. Alternatively, the number of monomers in a polymer (also a measure of size) can be determined as a function of the number of monomer-dependent conductance changes for a given polymer traversing the substrate. The number of monomers may not correspond exactly to the number of conductance changes, because there may be more than one conductance level change as each monomer of the polymer passes sequentially by the detector. However, there will be a proportional relationship between the two values, which can be determined by comparison against a standard of known composition. The mixture of polymers does not need to be homogeneous, since only one molecule interacts with the substrate at a time. It is possible to obtain a time distribution of molecules in a mixture and/or sequence data for multiple polymer molecules in the mixture.

The previously described methods rely on an aperture in the solid-state structure through or past which the polymer molecule traverses in order to obtain information regarding the polymer characteristics. It is contemplated that methods may be used to cause the molecule to traverse a small region of the solid-state substrate, i.e., a solid-state layer, without the use of an aperture.

In one such embodiment of the invention, a small region or feature may be defined on a solid-state substrate. Potential gradients or other factors are used to constrain the polymer within the limited region of the substrate. For example, a polymer molecule can be moved along a narrow or v-shaped trench, which confines the molecule laterally by application of the appropriate voltage gradient. Referring now to FIG. 10A, a molecule 120 can be moved laterally along a narrow or v-shaped trench 122 in an insulating substrate 123 by application of a voltage gradient between negative electrode 124 and positive electrode 126 or reversed depending on the charge of the polymer being moved. The trench 122 is filled with a weakly conductive liquid, e.g., a dilute salt solution (1–1000 mM KCl, preferably 1–100 mM KCl). Electrodes 124, 126 are in contact with the conductive fluid and may be located, for example, on a glass cover plate 128, positioned over the trench. The molecule can be confined to move along the bottom of the trench by virtue of trench size, or by application of an other independent voltage gradient orthogonal to the first gradient. The orthogonal potential's function is to keep the molecule pinned to the bottom of the trench while the first voltage gradient moves the molecule from one portion of the trench to another. The molecule advances in single file order because it is constrained laterally within the confines of the trench and possibly also vertically constrained by the orthogonal potential. Current is measured between electrode 129 (at zero potential), located on the glass cover plate, and electrode 125 embedded in the insulating substrate 123 and positioned immediately below and projecting above the bottom of the trench. Electrode 125 may be a metal tip of very small dimension, located at a point at the bottom of the trench to interact with the molecule as it passes. Thus, the tunneling current or ionic current detected as a function of time provides information regarding the presence, size and sequence of the molecule. In operation, only a single vessel is required to contain the polymer solution. Suitable trenches may be formed using the methods described in co-pending application entitled "Control of Solid State Dimensional Features", filed on even date herewith and which is incorporated by reference.

Figure 10B:
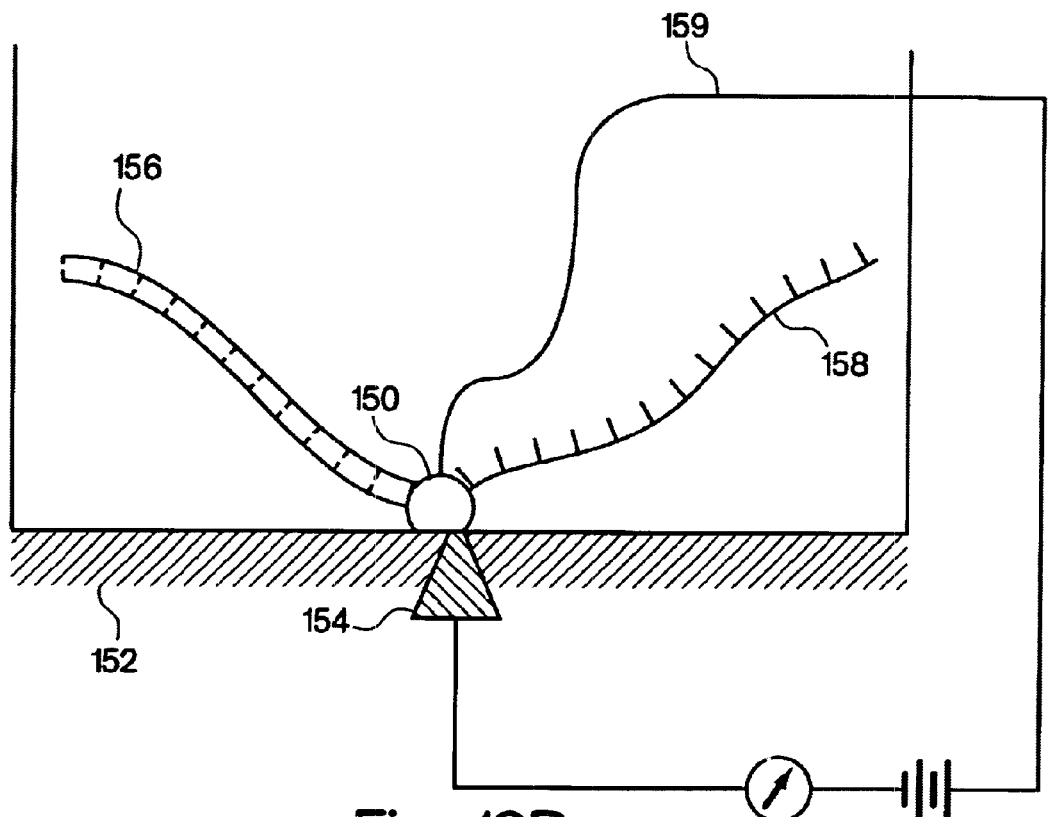
FIGS. 10 A–B illustrate a solid-state substrate of the invention used to evaluate polymer molecules.
Figure 10A:
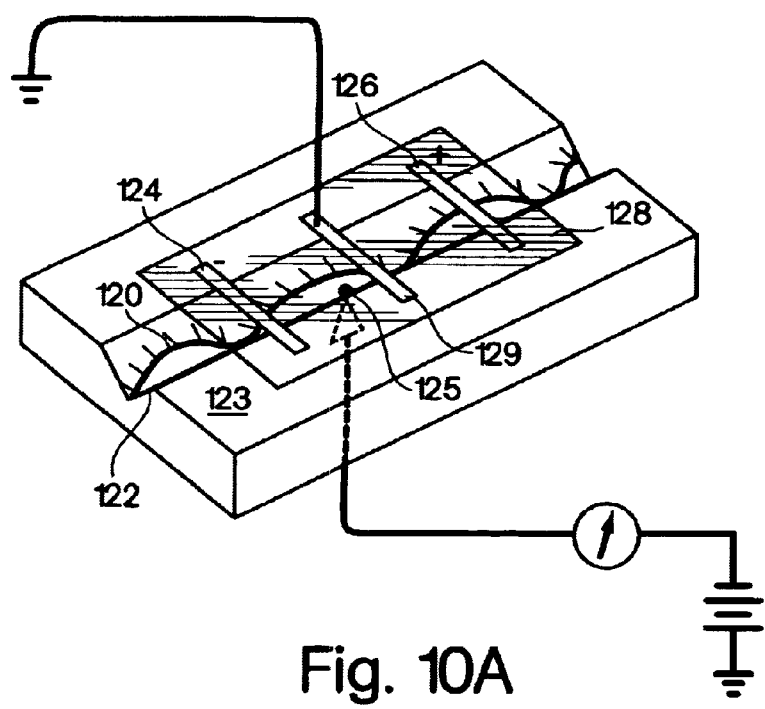

FIG. 10B illustrates yet another way to move a molecule linearly across a solid-state substrate surface. Translocation of molecules by using biological motors (e.g. a polymer replicating enzyme) through nanoscale apertures in the solid-state aperture is discussed below. The polymer can be induced to interact with or traverse the surface of the solid-state substrate by a polymerase or other template-dependent polymer replicating catalyst linked to the substrate which draws the polymer across the surface of the substrate as it synthesizes a new polymer from the template polymer. Alternatively, the polymer can be induced to interact with or traverse the surface of the solid-state substrate by an exonuclease or other template-dependent monomer cleaving catalyst linked to the substrate which draws the double-stranded polymer across the surface of the substrate and releases a single strand of DNA. The polymer replicating catalyst or the exonuclease can be attached to a surface using well-known methods, for example, by chemical attachment to the silicon nitride surface.

In one embodiment, a polymerase, which catalyzes the formation of a double-stranded DNA from a template DNA strand, is attached to the surface of the solid-state substrate. The solution contacting the substrate is provided with single strand DNA, primer and nucleic acids, that is, the materials necessary to replicate the existing single strand DNA. A nanometer scale electrode, e.g., a metallic tip, is positioned at the entrance of the polymerase, so that, as the DNA strand is drawn forward and into the polymerase for replication, it passes over and interacts at the electrode.

In another embodiment, shown in FIG. 10B, an exonuclease 150, which catalyzes the cleavage of nucleotides sequentially from the free end of a linear nucleic acid substrate to form a single strand DNA, is attached to the surface of the solid-state substrate 152. A nanometer scale electrode 154 is positioned at the far end of the exonuclease, so that, as the double-stranded DNA strand 156 is sequentially drawn forward and cleaved, the resulting single strand DNA 158 passes over and interacts at the electrode. A suitable electrode 159 in an ionic solution containing the substrate/exonuclease complex completes the circuit, and changes in current amplitude are an indication of characteristic polymer properties.

An "exonuclease" is an agent that cleaves nucleotides sequentially from the free ends of a linear nucleic acid substrate. A "polymer replicating polymer," is an agent that can catalytically assemble monomers into a polymer in a template-dependent fashion, i.e., in a manner that uses the polymer molecule originally provided as a template for reproducing that molecule from a pool of suitable monomers. Such agents include, but are not limited to, nucleotide polymerases of nay type, e.g., DNA polymerases, RNA polymerases, tRNA and ribosomes. The details involving selection of polymerase and appropriate conditions for use are discussed herein below.

Use of solid-state membranes and solid-state substrates provides several advantages over the prior art protein channel nanopores. Solid-state membranes and substrates are robust, can be prepared in bulk, stored indefinitely, and can be fashioned with very low capacitance because the membrane may be very thick except for the very small area immediately bordering the aperture. Furthermore, as is described in detail herein, an aperture in a solid-state material may be prepared using techniques which allow precise control of fine features of the aperture, including but not limited to, aperture diameter, contour, and channel length. The apertures may be fabricated with dimensions appropriate to detect the features of only one nucleotide at a time.

Solid-state apparatus of the invention may be prepared from robust materials capable of withstanding whatever chemical or temperature environments are required for successful evaluation of the molecule, and in particular, to withstand whatever temperature and chemical treatments are required to eliminate interference from polynucleotide secondary structure. Native single-stranded DNA cannot be pulled through the 1.5–2.0 nm channel that is suitable for individual nucleotide detection unless its secondary structure such as hairpin loops, are melted by high temperatures, chemical denaturants, or pH extremes. Because the midpoint melting temperature for native DNA is commonly about 70° C. at 0.1 M salt solution, an aperture in a robust substrate is required, which is capable of tolerating heat and denaturants sufficient to eliminate base pairing and secondary structure. The protein channels in delicate lipid bilayers do not tolerate these conditions. The use of heat- and chemical-tolerant solid-state materials for the substrate overcomes the limitations associated with protein channel membranes.

The solid-state substrates also provide an advantage over lipid bilayer membranes in situations where high salt content is used, such as in a PCR process. The present method is ideally suited to real time and rapid quantitative measurement of DNA concentration between cycles of amplification in the PCR process. PCR typically operates at ionic strengths below 100 mM, but suitable protein channels that have been used for polymer characterization do not perform correctly (e.g., they gate) at ionic strength below 500 mM, making them inappropriate for this application. Solid-state substrates lend themselves readily to such applications.

According to the invention, a method and apparatus are provided in which the nucleotide being characterized spends adequate time in the aperture channel to allow accurate measurement of ionic or electronic current. With voltage gradients adequate to prevent accidental backward diffusion of the DNA or RNA molecule (e.g., 100–150 mV), the polymer molecules may traverse through the aperture at rates that can exceed 1 nt/$\mu$s. Regardless of how perfectly current can be measured on the microsecond scale, the precision in the measurement of the change of the number of ions that flow will be the standard deviation of that number divided by the mean. Because differences between one DNA base and its neighboring base is measured, and because about 130 ions/$\mu$s has been found to be the current during occupancy by any base, the measurement of precision can not in general be better than about 10%. To comfortably measure what is estimated to be as little as a 1% difference in current reduction from nucleotide to nucleotide, the rate of DNA movement must be slowed by a factor of about $10^2$, or 100. Alternatively, the detection current may be increased by a similar amount, or 100-fold.

Hybridization-induced control of polymer molecule translocation. According to the present invention, reductions in DNA passage rate may be achieved by use of double-stranded, rather than single-stranded DNA (or RNA), which requires separation into individual strands before being admitted into the aperture for testing.

The rate of DNA movement through an aperture is slowed significantly when double-stranded, rather than single-stranded DNA (or RNA-DNA hybrid, etc.) is used. Specifically, if one applies a voltage gradient to a double-stranded DNA solution that is adequate to pull DNA through an aperture, but that aperture is too small to admit hybridized DNA, it is possible to separate the hybridized DNA, that is, to pull one of the strands of the initially double-stranded DNA apart from its complementary strand. A 100–150 mV gradient (equivalent to ca. $2 \times 10^{-13}$ ergs) can be used to pull single-stranded DNA without secondary structures through such channels.

Figure 11:
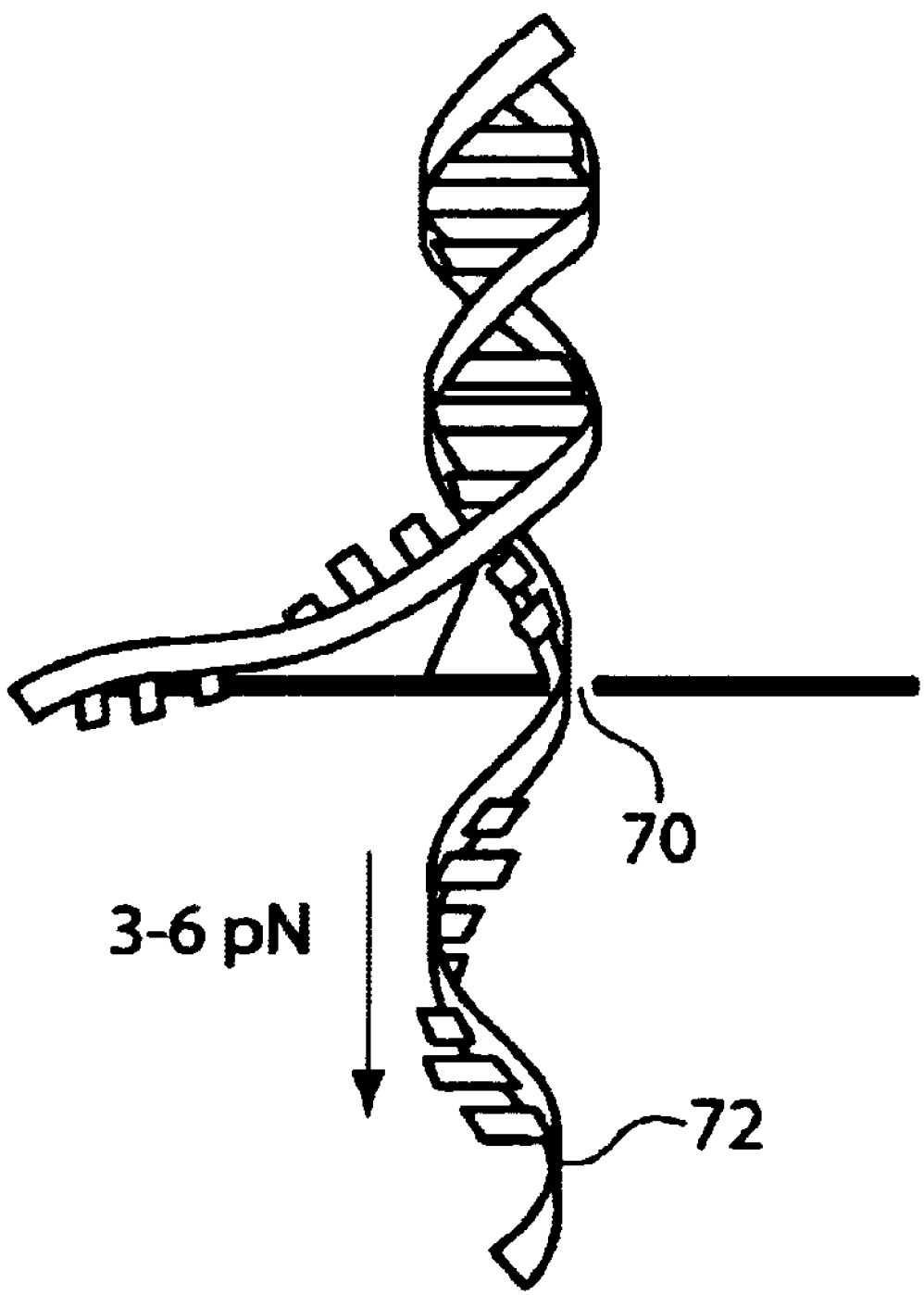
FIG. 11 is pictorial illustration of the separation of complementary polynucleic acid strands according to the method of the invention.
Figure 12A:
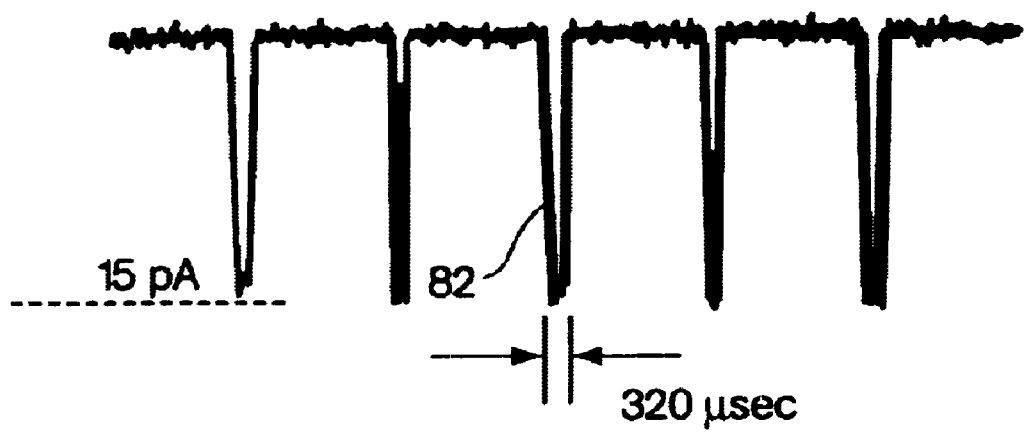
FIG. 12 is a plot of current vs. time for (A) a single-stranded poly[dA] molecule and (B) a double stranded poly[dA]-poly[dT] molecule as it is drawn through a *Staphylococcus aureus* α-hemolsin channel in a lipid bilayer.
Figure 12B:
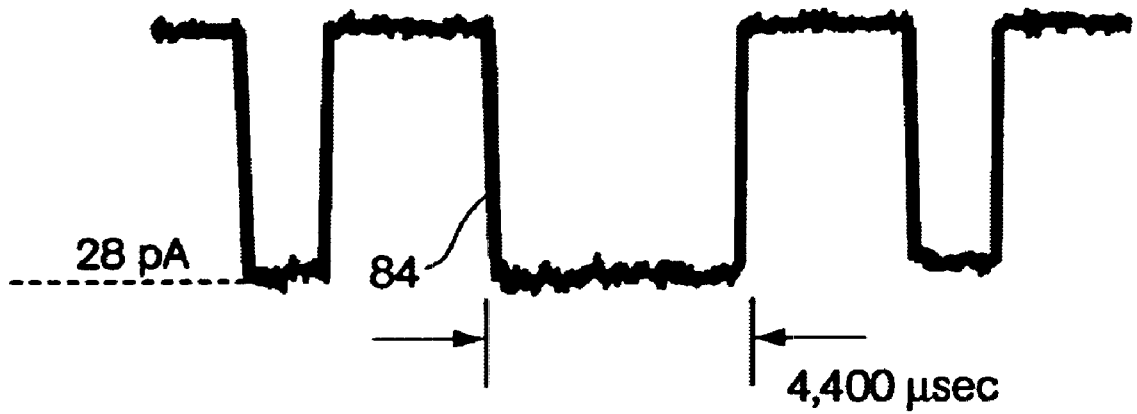

In this scenario, as shown in FIG. 11, the aperture 70 acts as a wedge to effect separation of the two strands 72 and 74. Because the present invention allows precise control of the aperture geometry, it is possible to use an aperture that facilitates the separation of double-stranded DNA. Application of a voltage gradient across the membrane creates a force, which pulls the single strand of DNA away from its complement and through the aperture one base at a time. The slowing effects of using double-stranded DNA as opposed to single-stranded DNA have been demonstrated for a protein channel pore. Similar results are expected with use of a solid-state aperture. On average, the single standard polynucleotides consisting of 100 adenine bases translocate through the protein channel in about 320 $\mu$sec (3.2 $\mu$sec/base) (FIG. 12). With reference to FIG. 12, a single-stranded poly[da] polynucleotide was first made to traverse an $\alpha$-hemolsin channel by application of a voltage gradient of 120 mV. The polynucleotide has a residence time in the channel of 320 $\mu$sec (see, current blockade 82, FIG. 12A). A hybridized polynucleotide was obtained by combining the poly[da] with its complement poly[dT] strand and the double-stranded poly[dA]-poly[dT] was pulled through the channel under a voltage gradient of 160 mV. Note that even at the higher applied voltage gradient, the DNA strand traversed the channel at a slower rate. The duration of one of the channel blockades is increased from 320 $\mu$sec to 4,400 $\mu$sec and the current that flowed during the blockade was increased from 15 pA to 28 pA (see, current blockade 84, FIG. 12B). Both the increase duration of the blockage, indicative of slower polymer traverse, as well as the greater current flow, the consequence of using a high voltage gradient, can contribute to greater precision in the measurement of current flow during channel occupancy of a polymer molecule.

Without being bound to any particular theory or mode of operation, the inventors herein recognize that greater voltages were likely needed to pull the double-stranded polynucleotide (poly[dA]-poly[dT]) through the pore because the lower gradients used with a single-stranded polynucleotide did not pull the molecule strongly enough and rapidly enough to break the nucleotides apart one at a time. Thus, with poly[dA] [dT] at lower potential gradients, little or no polymer traverse was seen and only single strand overhangs from the double stranded material were pulled into the channel, creating what has been identified as a "permablock." When the single strand overhang was drawn into the aperture, the double-stranded DNA portion of the molecule followed and became stuck because the double stranded portion was too wide to fit into the channel and the voltage gradient was too weak to pull the two strands apart within a limited amount of time (here the time was set at 5 msec). Only when the voltage gradient was increased to ca. 160 mV could the rest of the DNA strand that had initially been captured by the channel be pulled across the channel without pausing or creating permablocks longer than 5 msec. Similar observations have been made with G-C base pairs, which further slow the rate of DNA translocation.

The invention takes advantage of the different polymer behavior of single-stranded DNA and double-stranded DNA at different applied potentials to provide a method of individually monitoring discrete polymer monomers, that is, to provide a method of evaluating a polymer molecule that has sufficiently high resolution to obtain information regarding individual molecules.

According to the method of the invention, the polymer molecule is advanced in a ratchet-like or sequential manner across the aperture by applying a rapidly pulsating voltage gradient. Typically, one would apply a voltage of ca. 100–120 mV to draw the single strand overhang into the pore and keep it in position under tension for 200–600 microsec ($\mu$sec), and then apply a 125–600 mV for 0.1–2.0 $\mu$sec to dissociate one additional nucleotide pair and pull the DNA forward 1 base. This alternate application of low, then high, voltage would be repeated until the entire length of the DNA strand was "stepped" through the channel one base at a time. The duration of the high and low voltage pulses need not be the same. For example, a low voltage could be maintained until the electrical signals were unambiguous while the high voltage pulse could remain uniformly brief. Alternatively, software control could be implemented to decide the length of each low voltage session required to amass sufficient data to satisfy a predetermined probability of a "correct" read of the base lodged at the reading point in the channel.

The first voltage, e.g., 120 mV, is sufficient to cause a single-stranded polynucleotide to enter the channel and to largely prevent its backwards diffusion or movement, but insufficient to melt any double-stranded portions of the molecule. The second voltage, e.g., 125–160 mV, is greater than the first voltage and sufficient to rapidly separate the single strand from its complementary strand, so that it can move through the channel. Because of the oscillation between voltages that hold the polymer immobile within the channel and voltage that break up nucleic acid base-pairing to allow the molecule to advance within the channel, the DNA molecule is advanced stepwise through the channel and the opportunity to monitor each individual monomer's effect on ionic or electronic current is enhanced.

Such rapidly pulsating voltages can only be achieved in this system if the capacitance of the system (substrate and aperture) is generally small enough to allow for the desired rate of voltage fluctuations. In particular, it is desired that the capacitance be less than 0.1 pF, and that the total system, including the membrane, be capable of full discharge in the time scale of less than about 200 nsec. The solid-state membrane system of the invention provides a low capacitance system not previously available.

It should also be apparent that this method might be applied to detect regions of hybridization of a polynucleotide strand. The double-stranded regions may be intermolecular (hybridization between two nucleic acid molecules) or intramolecular (hybridization between portions of the same molecule). For example, the method may be used to detect the presence of hairpin loops in a polynucleotide strand, since the time associated with a current blockade of a strand with a hairpin loop would be expected to be much larger than that of a strand lacking a hairpin loop. The method may also be used to identify regions of hybridization on the polynucleotide strand. For example, a short primer may be added to a polynucleotide solution. Those polynucleotides capable of hybridizing with the primer will be identified because of the longer current blockade time as they traverse the aperture. Complete analysis of such signals could take into account the conditions of hybridization (salt, temperature, pH, etc.), the percentage of events whose positions are shifted to longer duration times, and their peak duration. Analysis provides comparative and quantitative estimates of the number of hybridizing molecules (e.g., concentration of reactants) as well as the measure of the binding energies involved in hybridization.

Biological motor-control of polymer molecule translocation. According to the present invention, reductions in DNA passage rate also may be achieved by using a biological motor to pull the DNA (rather than pull the DNA under an applied potential gradient) through the aperture. Although it is observed that the rate at which DNA is drawn through a protein channel varies with applied voltage, it is not thought practical to reduce the rate of DNA movement in this manner. The small voltage gradient required to achieve acceptable DNA translocation rates would severely compromise unidirectional movement of the polynucleotide through the channel. Reducing voltage would also reduce current, making detection between small differences in current levels very difficult.

Polymerases are efficient biological motors that can exert up to 10–20 pN forces by moving on DNA, and this may be used to control the rate of polymer movement through the aperture. Robust polymerases may provide a 3- to 4-order reduction in the rate of DNA movement through the aperture, while their ratchet-like activity decreases the probability of backward movement of the DNA in the aperture. Several commercially available, well-characterized polymerases, exonucleases and single strand helicases, including robust motors derived from thermophilic bacteria, are considered candidate motors. Polymerases of interest include the Klenow fragment of DNA polymerase I (Pol I), chosen because it may be used under more moderate conditions tolerated by lipid bilayers, and the similar Stoffel fragment of Taq polymerase. Because it tolerates high temperatures, and because it has evolved to move on a single-stranded DNA, Taq polymerase is a preferred polymerase of the invention. Polymerases that tolerate high temperatures are preferred because double-stranded DNA, hairpin loops, etc. may have to be melted prior to evaluation to obtain the single strand or to remove secondary structure.

Figures 13A, 13B:
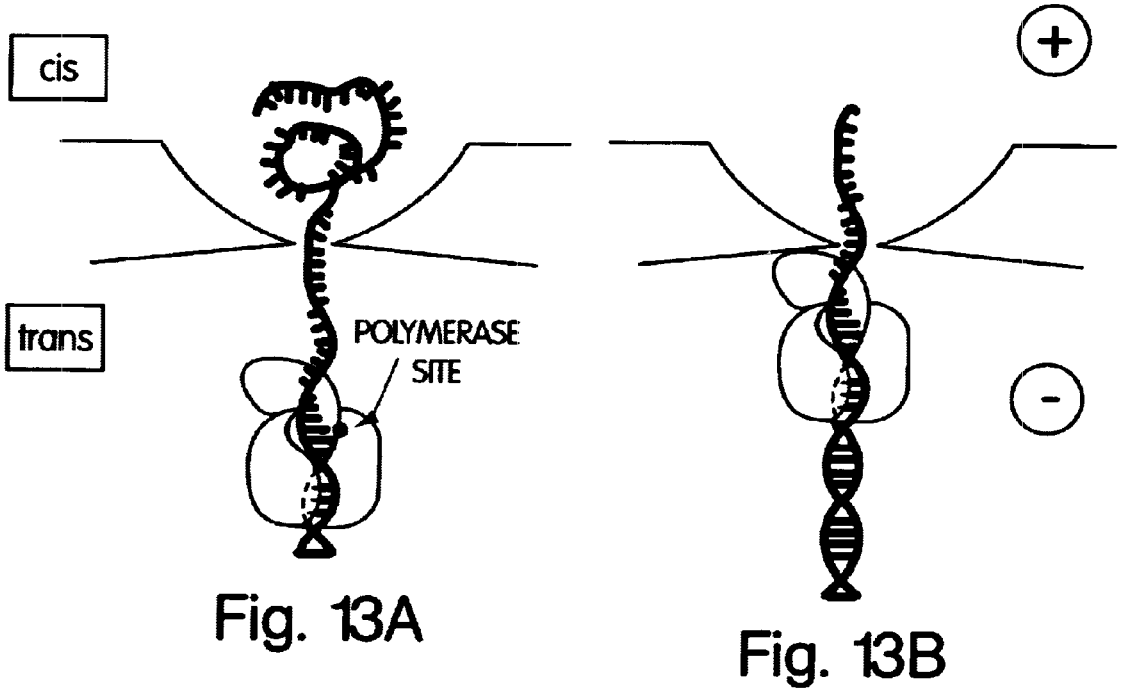
FIGS. 13 A–B are illustrations of a polymerase pulling DNA through an aperture in a solid-state membrane.

In one embodiment, single-stranded DNA is introduced into the cis side of the solid-state substrate, and primers, substrates and polymerase are placed on the trans side of the substrate. A small 3'-length of DNA (e.g., 15–20 nucleotides) begins to diffuse through an aperture in the substrate and is rapidly primed and then acted upon by polymerase in the trans chamber. See, FIG. 13A. Since optimal binding of polymerase to DNA requires at least 10 nt of primer-template duplex, use of brief voltage pulses (trans chamber positive) assures that a 15–20 nt length piece of DNA protrudes through the channel so that it can be primed and acted upon by the polymerase. During the ensuing replication, the polymerase moves 3' to 5' on the template strand until it runs into the aperture, as is shown in FIG. 13B. With an aperture size just large enough to permit passage of single strand DNA but not the polymerase, the working polymerase pulls the single strand of DNA through the aperture at its usual (slow) rate that characterizes its activity, e.g., about 1 nucleotide/20 ms. This rate is three orders of magnitude slower than the rate that can be achieved by pulling single strand DNA through an aperture with a voltage gradient alone. Once the template is primed, a voltage of opposite polarity (cis chamber positive) is applied to drive ions through the now-DNA filled aperture (see, FIG. 13B) in the trans to cis direction, i.e., opposing the movement of the DNA and thus placing the DNA under tension and reduce the effects of thermal motion in the DNA. Assuming the polymerase exerts a 10 pN force on the DNA, a 100 mV/5 nm field pulling the DNA in the direction opposite the polymerase could be tolerated, since the countervailing voltage exerts a force of only 3 pN.

In other embodiments of the invention, the DNA and primer are mixed together in the cis chamber, the unprimed end of the DNA is pulled through the aperture under voltage gradient, and then pulled back into the cis chamber (against the countervailing 100 mV gradient) when polymerase is added to the cis solution. In this embodiment, sequencing takes place as the DNA is pulled back into the cis chamber.

There are two factors to consider in the design of a polymerase-moderated evaluation of DNA. First, there may be concern that the frequent 3 nm movements of the growing 3' end of the primer strand from the polymerase site to the editing 3'–5' exonuclease domain would jiggle this single-stranded DNA back and forth in the aperture channel, thereby reducing the accuracy of the measured current changes. Fortunately, little of this movement is expected to shift the front end of the polymerase along the length of the single strand template.

Second, Taq polymerase and Pol I polymerase are not progressive, and tend to dissociate and reassociate with the template-primer complex on average every 60 nucleotides. Other than a brief delay in sequencing, the dissociation should have little effect on the process since the duplex DNA, from which the polymerase dissociates (e.g., the portion of the DNA strand which has already passed through the apertures and which is double-stranded), is itself unable to move through the aperture as a double-stranded molecule, and the DNA is held in place by the countervailing voltage gradient until the polymerase reassociates and DNA movement continues.

Figure 14:
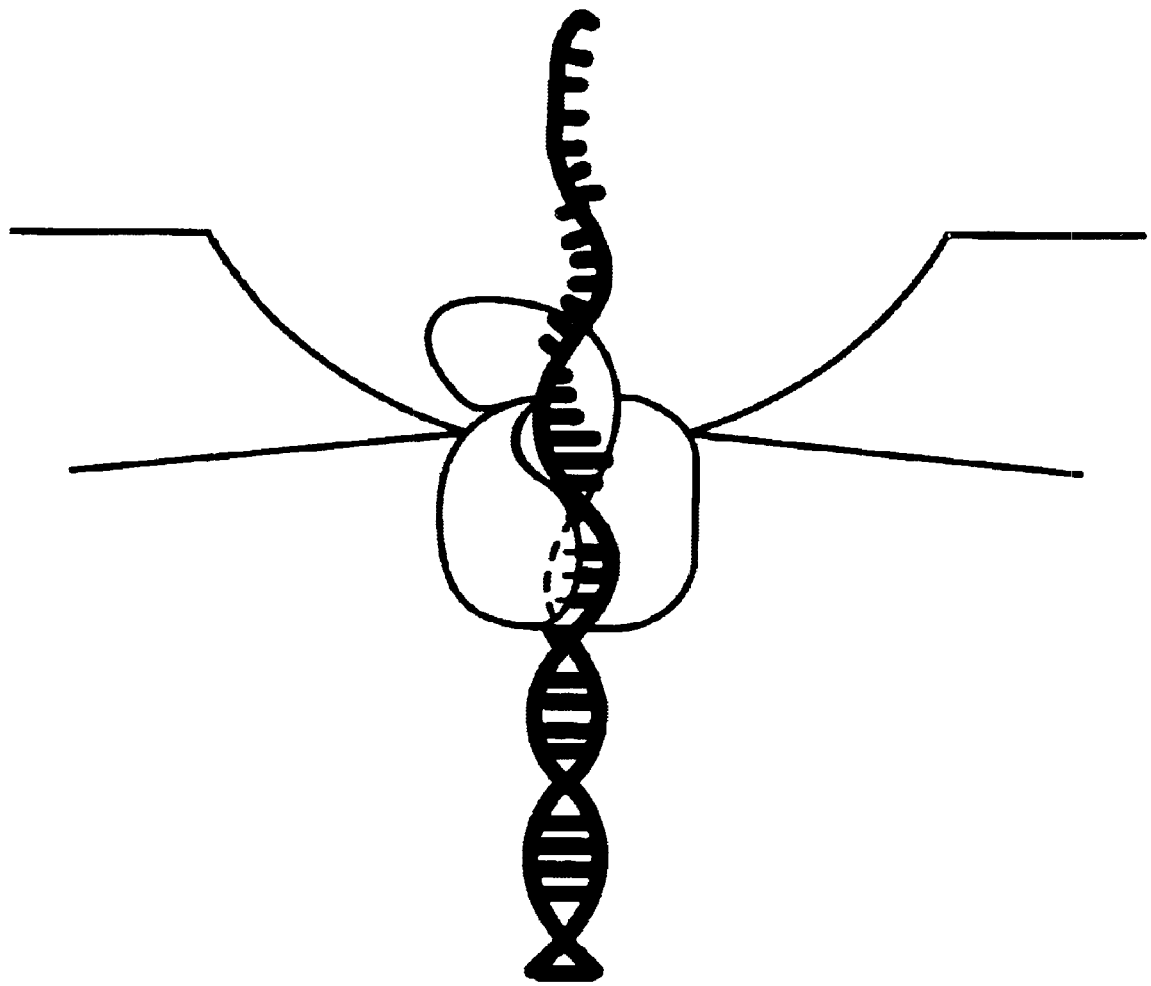
FIG. 14 is an illustration of a polymerase-solid state substrate composite which forms a constraining diameter within the polymer detecting DNA.

The movement of a polymerase toward the aperture through which protrudes a strand of DNA can also be used to position the polymerase at the aperture or part way into the aperture, as shown in FIG. 14. When fixed in position, by chemical crosslinking or by affinity binding to the aperture or some other means, the polymerase forms a protein-solid state composite. The composite provides a proteinlined channel with a self-contained motor to pull the DNA through at a slow and steady rate. In this embodiment, the constraining diameter may be a region of the channel defined by the polymerase, or it may be a portion of the aperture channel.

In one embodiment, the solid-state substrate is silicon-containing, e.g., $Si_3N_4$, and the polymerase is attached thereto by chemical attachment of nickel atoms deposited on the trans facing surface of the silicon nitride. A Taq polymerase modified to contain a suitable patch of histidine residues may be used for this purpose. Since the Stoffel fragment of Taq polymerase is routinely produced by expressing its recombinant cDNA in *E. coli*, and since those residues of Taq polymerase needed for activity have been mapped out in detail (see, A. Kornberg and T. A. Baker, *DNA Replication* W. H Freeman & Co. (1992); and Eom et al. *Nature*, 382:278 (1996)), an active Taq polymerase with a suitable histidine patch may be prepared for complexing with the nickel surface.

Since the template-primer duplex and the template bind in an accessible groove on the surface of Taq polymerase (see, Kornberg and Baker, supra), DNA that is being pulled through the Taq polymerase-solid state aperture composite is surrounded through about 300° by the surface of the polymerase groove and through the remaining 60° by a portion of the inner rim of the aperture. When an electric field is applied to this composite, the number of ions that can move through and along the unoccupied spaces of this polymerase-lined channel should be sensitive to the physical and chemical differences between bases and to the conformational movements of the polymerase. Sensitivity to the differences between bases should be maximal when the "front-end" region of the Taq polymerase fragment (region closest to the vestigial editing domain) is within the silicon aperture channel. In this position, the ion flow is restricted by the Taq groove, the aperture rim and single-stranded regions of the template DNA rather than the newly formed double-stranded regions of the DNA farther "back" on the polymerase. Therefore, fluctuations of current are a reflection of monomer composition and sequence.

A further advantage of fixing the polymerase at or in the aperture of the solidstate membrane is that the circumference of the aperture serves to hold the DNA in the polymerase cleft thus enhancing the processivity of the Taq polymerase enzyme.

Electron tunneling into polymer molecules. In another embodiment of the invention, using tunneling currents rather than ionic currents to sense the nucleotide bases as they move through or past the aperture can significantly increase the detection signal. Tunneling is the purely quantum mechanical effect that allows particles of nature to penetrate into regions of space that would normally be inaccessible by the principles of Newtonian classical mechanics. When tunneling, the quantum mechanical spatial wavefunction of a particle acquires an exponential form with a decay constant that depends on the square root of the particle mass and potential barrier inhibiting the motion. For charged particles, tunneling can be observed experimentally through electrical currents associated with their transport through classically forbidden regions. The small mass of an electron enhances the penetration into these regions and, hence, electronic rather than ionic conduction is the phenomena of interest.

While electron-tunneling spectroscopy has achieved atomic scale resolution of images, these techniques have not yet produced information regarding DNA sequence. Electron tunneling methods have been limited by problems of aligning the electrode tip with a DNA molecule immobilized onto a viewing surface.

In the method of the invention, the DNA traverses a spatially narrow region, which specifically favors the examination of a linear, single strand of DNA. Tunneling is considered a particularly preferred method of monitoring the passage of DNA through the aperture because tunneling currents associated with the operation of the tunneling microscope are in the 1–10 nanoamp range, which is two to three orders of magnitude greater than ionic conduction currents.

Figure 15:
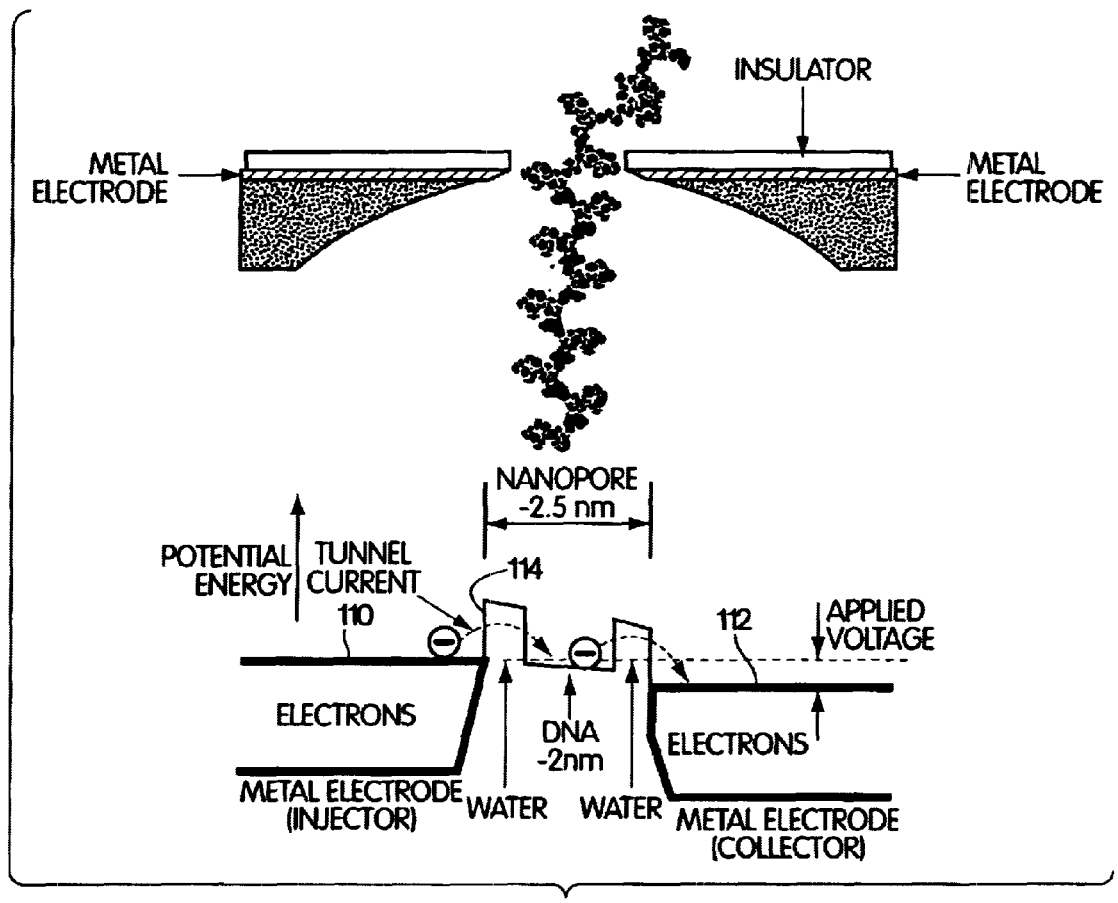
FIG. 15A shows a pictorial illustration of a DNA molecule traversing an aperture in a solid-state substrate of the invention.
FIG. 15B is a plot of the potential energy experienced by an electron in the vicinity of the electrodes and DNA-filled aperture.

FIG. 15A shows a pictorial illustration of a DNA molecule traversing an aperture in a solid-state membrane of the invention. Metal electrodes are deposited on the membrane on either side of the aperture and are in electrical communication with the aperture. A protective insulating layer may be deposited on the electrodes. The surface area of the electrode in contact with the aperture is quite small, making it a sensitive probe of the changes in the DNA composition as it traverses the aperture.

FIG. 15B is a plot of the potential energy experienced by an electron in the vicinity of the electrodes and DNA-filled aperture. In this figure, an electron 110 on the left is the source of conduction electrodes and is biased negatively relative to a collection electrode 112, which is on the right. In order to contribute to electronic conduction, an electron must overcome an energy barrier 114, which is characteristically several volts high. Classically this barrier totally inhibits direct electronic flow, but quantum mechanically, there is a finite possibility of electron transmission through the barrier. Assuming a barrier height of 2.6 eV and a conservative bias of 5 mV across a 0.5 nm thick barrier gives a current density of 10 $nA/nm^2$. A rough estimate for the area of a nucleotide base is 0.5 $nm^2$, yielding a rough estimate of 5 nA of net tunneling current. Higher tunneling bias voltages would yield greater currents. Embodiments that rely upon electronic tunneling for detecting the DNA molecule may use either a simple voltage gradient or a polymerase biomotor to move the DNA molecule through the aperture.

Figure 16A:
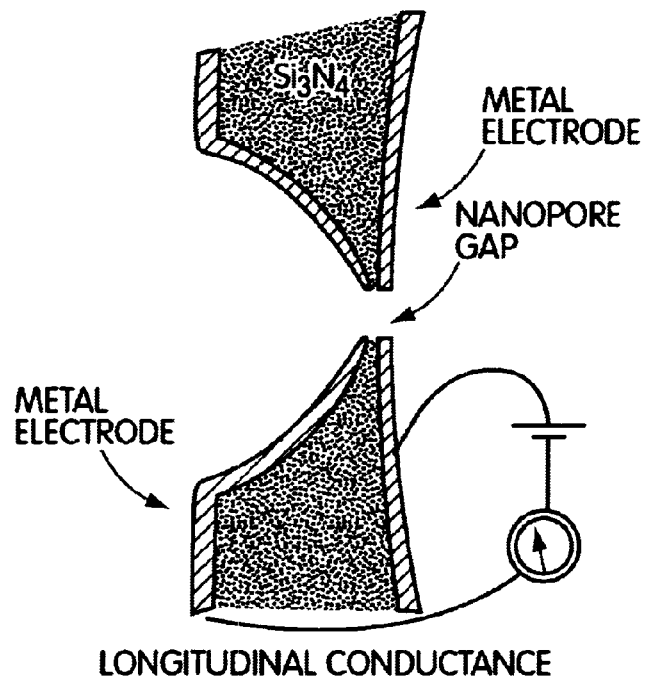
FIG. 16A is a schematic representation of a circuit for enabling longitudinal tunneling conductance measurements; and 16B is a schematic representation of a circuit for enabling transverse tunneling conductance measurements.

For applications in which an electron tunneling current measurement is employed, the aperture-containing membrane is configured in a circuit that applies a voltage bias between the tunneling electrodes and that enables measurement of the tunneling current indicative of molecular traversal between the electrodes. Connection to the membrane electrodes is made in any suitable conventional manner, e.g., by wire bonding, direct ionic contact with fluid or other suitable technique. FIG. 16A, is a schematic representation of a circuit for enabling longitudinal tunneling conductance measurements. Both surfaces of the solid-state membrane are metallized, so that the metallic injection and collection electrodes reside on opposite surfaces of the insulating solid-state membrane. A small gap through which tunneling current is monitored is formed within the aperture, and electrons tunnel longitudinally, parallel to the length of DNA in the channel. In some embodiments, only an injection electrode may be required, as the electronic current passing through the DNA will tend to transform itself into ionic conduction after it has passed through the aperture channel.

Figure 16B:
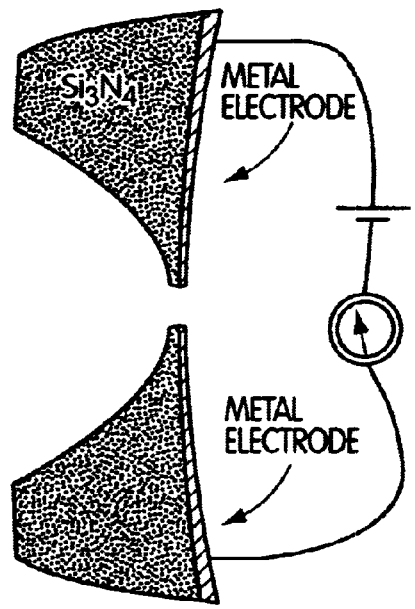

FIG. 16B is a schematic representation of a circuit for enabling transverse tunneling conductance measurements. In this arrangement, the electrodes are coated with an insulating layer at a location at a distance from the immediate region of the aperture to prevent ionic currents that could dominate the electrical signal. In each of these circuits, a voltage source is provided for applying a desired voltage bias between the tunneling electrodes to induce tunneling from one electrode through the solution and traversing molecule to the second electrode. For most applications, a voltage of, e.g., between about 50 mV and about 5 V is sufficient for inducing tunneling conditions. A tunneling integrating electrometer is further included in the circuit topology for measuring the tunneling currents. Preferably, the preamplifyer circuit enables electrical current measurement under tunneling conditions on a microsecond time scale. The output of the preamplifyer is directed to a measurement device, e.g., an oscilloscope, for monitoring the preamplifyer output. For many applications it can be convenient to direct the output voltage measurement of the preamplifyer to a computer for recording, given that discrete tunneling current measurements are sampled at an interval of, e.g., between about 3 microseconds and about 5 microseconds for many applications.

Due to this generally very short sampling interval, it is preferred that the tunneling current preamplifyer be characterized by an operational bandwidth that is commensurate with the expected sampling interval. For example, a preamplifyer bandwidth greater than about 1 MHz can be preferred for many applications. It is preferred in accordance with the invention to employ a symmetrical -preamplifyer topology like that taught by Denison in U.S. Ser. No. 09/502,134, filed Feb. 11, 2000, and entitled "Preamplifyer Topology," the entirety of which is hereby incorporated by reference.

This preferred preamplifyer topology employs dual, symmetric integration capacitors rather than a single integration capacitor as is conventional. By symmetrically charging and discharging the dual capacitor pair, "dead time" associated with integration capacitor-reset, and preamplifyer input transients are substantially eliminated. The symmetric charging and discharging of the integration capacitors also reduces the parasitic effects of dielectric absorption. Conventionally, an integration capacitor is initially discharged and then the preamplifyer output is periodically sampled and reset. In contrast, with the preamplifyer topology preferred in accordance with the invention, resets are eliminated by the symmetric capacitors, such that perpetual integration can be carried out. This enables very high speed, low noise integration operation.

It is to be recognized in accordance with the invention that this particular preamplifyer topology is not strictly required. It is preferred in accordance with the invention that a selected preamplifyer be characterized by an operational bandwidth that is commensurate with the detection or sequencing interval of a given application.

One advantage of the apparatus and method of the invention is that electrodes can be placed in the immediate vicinity of the aperture on the solid-state surface using standard semiconductor nanofabrication techniques. For example, thin film metal electrodes may be deposited using e-beam lithography or molecular beam epitaxy. FIGS. 16A and 16B illustrate two possible geometries contemplated for electronic atomic scale molecular detection of polymers drawn through nanoscale apertures.

The invention is described in the following examples which are presented for the purpose of illustration only, and which are not limiting of the invention.

EXAMPLE 1

This example describes an apparatus used in the measurement of molecular interactions of a single-stranded DNA molecule with a nanoscale aperture, 16 nm in diameter, in a solid-state $Si_3N_4$ substrate.

The apparatus was set-up as in FIG. 9, described above. A 1 M KCl solution was used in both chambers as the conductive liquid. A 50 mm thick silicon nitride layer was deposited by low pressure CVD on a silicon wafer and a hole was fabricated in the silicon nitride layer using the process outlined in FIGS. 4A–G. Specifically, a hole of the desired diameter was obtained by e-beam lithography and reactive ion etching.

A 5.7 kbase, single strand (ss) DNA was used. The ssDNA was complexed with a binding protein in order to increase its diameter to about 7 nm. Closed-circle single-stranded DNA from the bacteriophage PhiX174 was obtained from New England Laboratories (32 Tozer Rd., Beverly, Mass.) and made linear by annealing a short (22 nucleotides long) piece of complementary synthetic DNA to one specific site on the viral DNA in solution. The resultant double stranded region on the viral ssDNA provided a specific site that is recognized by, and binds to, a restriction enzyme (Ssp I; New England Biolabs) which cleaves the DNA molecule in solution under optimized conditions. Following the restriction enzyme digestion, the 5.3 kb linear ssDNA was isolated and stored as purified material.

SSB protein (obtained from Stratagene, 11011 N. Torrey Pines Rd., La Jolla, Calif.) was combined with purified 5.3 kb linear ssDNA in a buffered saline solution at a 1:10 (w/w) ratio of ssDNA:SSB, and incubated for approx. five minutes at ambient temperature before the introduction of the DNA/protein sample into the silicon nitride apparatus according to the method described by Tsurushita, N., H. Maki, and L. J. Korn, (Site-directed mutagenesis with *E. coli* DNA polymerase III holoenzyme. Gene 62: 135–139, 1988).

The apparatus was set up and aligned as described with respect to FIG. 9. Alignment was facilitated by use of a glass-bottom container with a light source located below the sample chamber. Once aligned, the funnel was flushed, first with methanol and then with 1 M KCl solution to wet the solid-state substrate and aperture surfaces. The holding vessel was filled with 1 M KCl solution and the funnel was filled with a 1 M KCl solution (3–5 ρL) containing the single-stranded DNA.

Figure 17A:
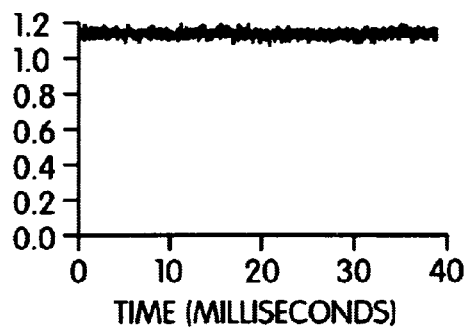
FIG. 17 is a current vs. time plot (A) in the absence of and (B) in the presence of a single strand DNA-binding protein complex under an applied voltage gradient of 200 mV.
Figure 17B:
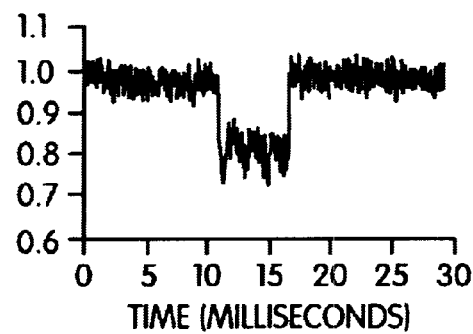

A 200 mV negative bias was applied across the substrate and dc ionic current was monitored. FIG. 17A is a plot of current vs. time in the absence of DNA, indicating substantially no disruption to ionic current flow. FIG. 17B is a plot of current vs. time in the presence of DNA, indicating multiple current diminution events. These current reductions with time that are observed with DNA and absent without DNA in solution are an indication of aperture-DNA interactions. The events are taking place on a microsecond-to-millisecond time scale. The duration and frequency of the current blockade events is commensurate with those observed for DNA of similar size and composition when protein channels are used.

EXAMPLE 2

This example describes an apparatus used in the measurement of molecular interactions of a double-stranded DNA molecule with a nanoscale aperture, 10 nm in diameter, in a solid-state $Si_3N_4$ substrate.

The apparatus was set-up as in FIG. 9, described above. A 1 M KCl solution was used in both chambers as the conductive liquid. A hole was fabricated in a 500 nm thick silicon nitride layer using the process outlines in FIGS. 4A–G. Specifically, a 500 nm thick silicon nitride layer was deposited on a silicon wafer and a 90 nm wide hole milled into the layer using a focused ion beam. The large, square hole was reduced to 10 nm in diameter by sputtering with argon ion beam at 3 KeV incident energy at 22° C.

A 6.4 kbase, double strand (ds) DNA in 1 M KCl solution was used. A cloning vector was isolated and purified in our laboratory as the source for 6.4 kb closed-circular dsDNA. This material was treated with a restriction enzyme (Ssp I; New England Biolabs) that cleaves the molecules at a single, sequence specific site in solution under optimized conditions. The resulting linear dsDNA was isolated and purified following restriction enzyme digestion.

The apparatus was set up and aligned as described with respect to FIG. 9. Alignment was facilitated by use of a glass-bottom container with a light source located below the sample chamber. Once aligned, the funnel was flushed, first with methanol and then with 1 M KCl solution to wet the solid-state substrate and aperture surfaces. The holding vessel was filled with 1 M KCl solution and the funnel was filled with a 1 M KCl solution 3÷5 ρL solution containing the double-stranded DNA.

Figure 18:
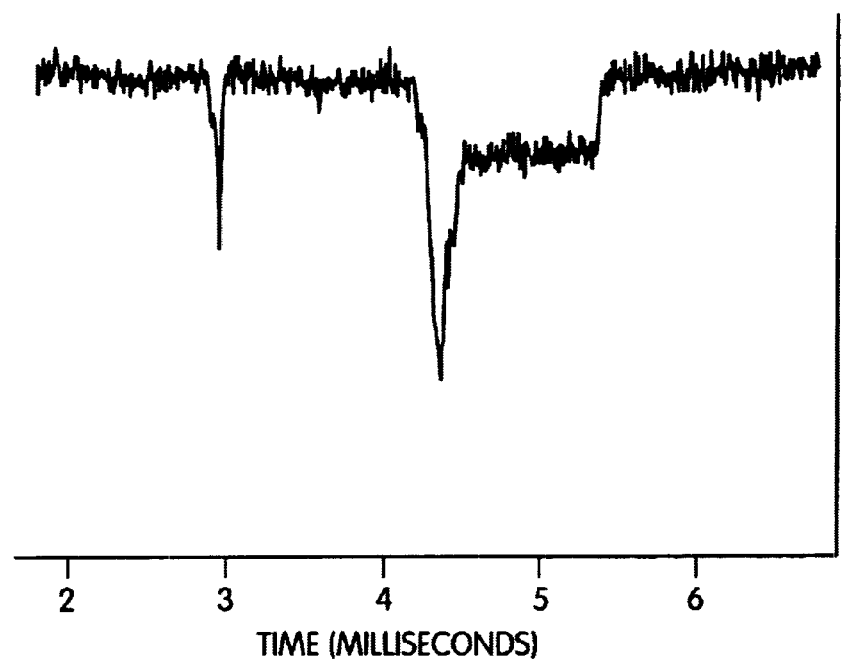
FIG. 18 is a current vs. time plot of a double strand DNA under an applied voltage gradient of 100 mV.

A 100 mV negative bias was applied across the substrate and dc ionic current was monitored. FIG. 18 is a plot of current vs. time in the presence of DNA, indicating multiple current diminution events. These current reductions with time that are observed with DNA and absent without DNA in solution are an indication of aperture-DNA interactions. The events are taking place on a microsecond-to-millisecond time scale. The duration and frequency of the current blockade events is commensurate with those observed for DNA of similar size and composition when protein channels are used.

EXAMPLE 3

This example describes an apparatus used in the measurement of molecular interactions of a double-stranded DNA molecule with a nanoscale aperture, 3 nm in diameter, in a solid-state $Si_3N_4$ substrate.

The apparatus was set-up as in FIG. 9, described above. A 1 M KCl solution was used in both chambers as the conductive liquid. A hole was fabricated in a 50 nm thick silicon nitride layer using the process outlined in FIGS. 4A–G. Specifically, a 50 nm thick silicon nitride layer was deposited on a silicon wafer and a hole of the desired diameter was obtained by e-beam lithography and reactive ion etching.

A 6.4 kbase, double strand DNA as in Example 2 in 1 M KCl solution was used. The apparatus was set up and aligned as described with respect to FIG. 9. Alignment was facilitated by use of a glass-bottom container with a light source located below the sample chamber. Once aligned, the funnel was flushed, first with methanol and then with 1 M KCl solution to wet the solid-state substrate and aperture surfaces. The holding vessel was filled with 1 M KCl solution and the funnel was filled with a 1 M KCl solution 3–5 ρL containing the double-stranded DNA.

Figure 19:
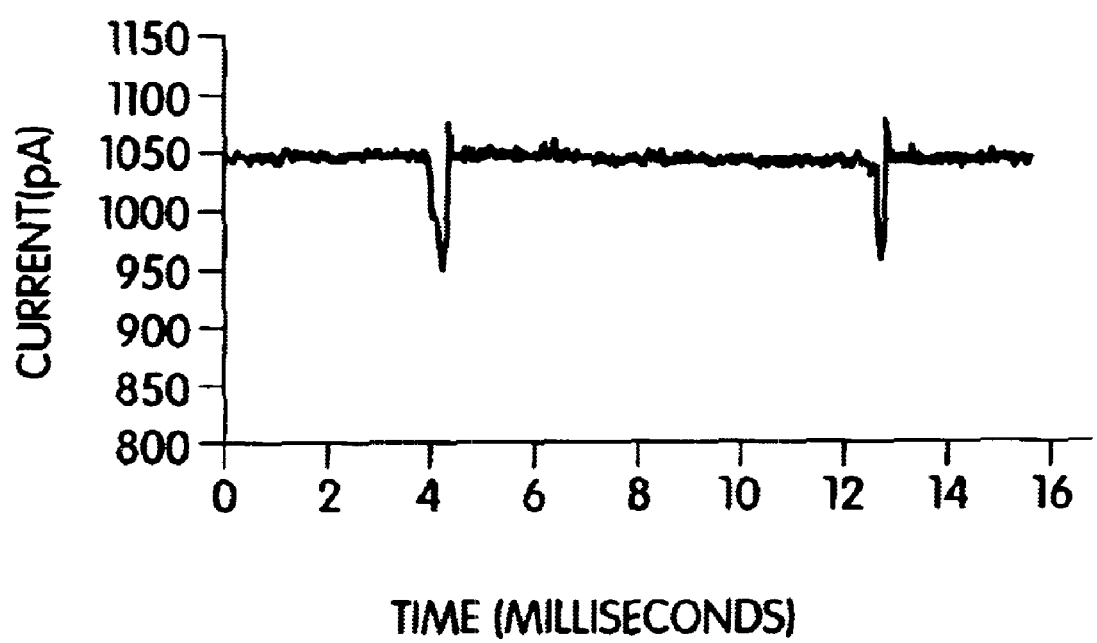
FIG. 19 is a current vs. time plot of a double strand DNA under an applied voltage gradient of 100 mV.

A 100 mV negative bias was applied across the substrate and dc ionic current was monitored. FIG. 19 is a plot of current vs. time in the presence of DNA, indicating multiple current diminution events. These current reductions with time that are observed with DNA and absent without DNA in solution are an indication of aperture-DNA interactions. The events are taking place on a microsecond-to-millisecond time scale. The duration and frequency of the current blockade events is commensurate with those observed for DNA of similar size and composition when protein channels are used.

What is claimed is:

1. An apparatus for use in evaluating a linear polymer molecule, comprising:

a vessel for holding a liquid containing a candidate polymer molecule;

a solid-state membrane containing an aperture therein, said aperture comprising a constraining dimension, wherein the aperture includes an entry port and an exit port defining a channel there between, and wherein the membrane is positioned to be contactable with a liquid in the vessel;

means for causing a candidate polymer molecule to linearly traverse the aperture; and a detector for detecting sensing time-dependent or monomer-dependent interactions of a candidate molecule with the aperture detector, said detector located in the aperture or on a face of the solid-state membrane.

2. The apparatus of claim 1, wherein the solid-state membrane comprises an electrically insulating material.

3. The apparatus of claim 1, wherein the channel is coated with an electrically insulating layer.

4. The apparatus of claim 1, wherein the channel is coated with a passivating layer.

5. The apparatus of claim 1, wherein the constraining dimension is located adjacent to, below, above or within the aperture.

6. The method of claim 5, wherein the detector comprises the constraining diameter of the aperture.

7. The apparatus of claim 1, wherein the constraining dimension is in the range of less than about 20 nm.

8. The apparatus of claim 1, wherein the constraining dimension is in the range of less than about 5 nm.

9. The apparatus of claim 1, wherein the constraining dimension is in the range of about less than 0.1–2 nm.

10. The apparatus of claim 1, wherein the constraining dimension comprises a feature integral with the aperture and tapering acutely to form a point of constriction in the aperture channel.

11. The apparatus of claim 10, wherein the taper is curvilinear.

12. The apparatus of claim 10, wherein the taper varies in acuteness along the length of the channel.

13. The apparatus of claim 10, wherein the feature is located at the exit or entry port of the aperture.

14. The apparatus of claim 10, wherein the feature is located within the channel of the aperture.

15. The apparatus of claim 1, wherein the constraining dimension extends through the channel for a length that is in the range of 0.1 to 10 nm.

16. The apparatus of claim 1, wherein the constraining dimension extends through the channel for a length that is in the range of 0.1 to 5 nm.

17. The apparatus of claim 1, wherein the solid-state membrane is selected from the group consisting of inorganic compounds, organic and inorganic polymers and glasses.

18. The apparatus of claim 1, wherein the solid-state membrane is selected from the group consisting of silicon nitrides, silica, alumina.

19. The apparatus of claim 1, wherein the solid-state membrane has a thickness in the range of about 10 nm to about 1 mm.

20. The apparatus of claim 1, wherein the solid-state membrane has a thickness in the range of about 50 nm to about 100 nm.

21. The apparatus of claim 1, wherein the solid-state membrane has a capacitance of less than about 0.1 pF.

22. The apparatus of claim 1, wherein the detector comprises first and second electrodes on a face of the solid-state membrane adjacent to the aperture and in electrical communication with the channel.

23. The apparatus of claim 22, wherein the first and second electrodes are on the same side of the solid-state membrane.

24. The apparatus of claim 22, wherein the first and second electrodes are on opposing sides of the solid-state membrane.

25. The apparatus of claim 22, wherein said electrodes comprise a conductive metal layer deposited on the solid-state membrane.

26. The apparatus of claim 22, further comprising:
at least one insulating layer adjacent to the first and second electrodes.

27. The apparatus of claim 1, wherein the apparatus further comprises a monitoring means, and the monitoring means comprises an ammeter or an electrometer.

28. The apparatus of claim 1, wherein the means for causing a candidate polymer molecule to traverse the aperture is selected from the group consisting of voltage gradient means and biomotors.

29. The apparatus of claim 1 or 22, further comprising:
a substrate supporting the solid-state membrane.

30. The apparatus of claim 1, wherein a polymer replicating catalyst is in contact with the aperture.

31. The apparatus of claim 30, wherein the polymer replicating catalyst is located adjacent to, above, below, or within the membrane aperture.

32. The apparatus of claim 31, wherein the polymer replicating catalyst is the constraining dimension diameter feature.

33. The apparatus of claim 1, wherein the detector comprises an electrode pair located on opposing faces of the solid-state membrane, and the detector detects interactions of the electrode pair with a candidate molecule located between the electrode pair, and wherein the constraining dimension located at or between the electrode pair.

34. The apparatus of claim 33, wherein a detection signal arises from longitudinal electron tunneling along the length of the aperture channel.

35. The apparatus of claim 1, wherein the detector comprises an electrode pair located on a face of the solid-state membrane spaced apart from one another at opposing sides of the entry port or the exit port of the aperture.

36. The apparatus of claim 35, wherein the electrode pair comprises the constraining dimension.

37. The apparatus of claim 33 or 35, wherein the apparatus further comprises a dielectric layer disposed on each of the electrodes of the electrode pair.

38. The apparatus of claim 35, wherein a detection signal arises from transverse electron tunneling across the aperture.

39. An apparatus for use in evaluating a linear polymer molecule, comprising:
a first vessel having a first inlet therein;
a second vessel having a second inlet therein;
an elongated member having first and second ends, each end in sealing communication with the respective inlets of the first and second vessels;
a solid-state membrane containing an electrically insulating aperture therein disposed in the first end of the elongated member, wherein the aperture includes an entry port and an exit port defining a channel there between, and the membrane is positioned to be contactable with a liquid containing a candidate polymer molecule in the first vessel;
means for causing a candidate polymer molecule to linearly traverse the aperture; and
a detector for sensing time-dependent or monomer-dependent interactions of a candidate molecule with the detector, said detector located in the aperture or on a face of the solid-state membrane .

40. A method for evaluating a polymer molecule, the polymer molecule including linearly connected monomer residues, comprising:
contacting a liquid containing a polymer molecule with an insulating solid-state substrate having a detector capable of detecting polymer molecule characteristics;
causing the polymer molecule to traverse a limited volume on the solid-state substrate so that monomers of the polymer molecule traverse the limited volume in sequential order, whereby the polymer molecule interacts sequentially with the detector, whereby the detector comprises an electrode pair, and electron current is detected as the monomer traverses the limited volume and data suitable to determine polymer molecule characteristics are obtained.

41. The method of claim 40, wherein the limited volume of the solid-state substrate is a groove on the solid-state substrate surface, and the detector is located at the base of the groove, whereby the polymer molecule traverses the length of the groove.

42. The method of claim 40, wherein the polymer molecule is selected from the group consisting of polynucleic acids, DNA and RNA.

43. The method of claim 40, wherein the detector is located on the substrate surface, and further comprising:
   a polymer replicating catalyst attached to the solid-state surface adjacent to the detector, whereby the polymer molecule is acted upon by the polymer replicating catalyst, so that the polymer molecule interacts sequentially with the detector as it advances through the polymer replicating catalyst.

44. The method of claim 43, wherein the liquid is a solution further including reagents necessary to replicate the polymer molecule.

45. The apparatus of claim 40, wherein the constraining dimension is located adjacent to, below, above or within the aperture.

46. A method for evaluating a polymer molecule, the polymer molecule including linearly connected monomer residues, comprising:
   contacting a liquid containing a polymer molecule with an insulating solid-state membrane having an aperture therein, wherein the aperture includes an entry port and an exit port defining a channel there between,
   causing the polymer molecule to traverse the aperture of the membrane, whereby the polymer molecule interacts sequentially with a constraining dimension in, of or at the aperture and data arising from time-dependent or monomer-dependent interactions of a candidate molecule with a detector located in the aperture or on a face of the solid-state membrane are obtained.

47. The method of claim 46, wherein the solid-state membrane comprises an electrically insulating material.

48. The method of claim 46, wherein the aperture channel is coated with an electrically insulating layer, or a passivity layer.

49. The method of claim 46, wherein the constraining dimension is in the range of less than about 20 nm.

50. The method of claim 46, wherein the constraining dimension is in the range of less than about 5 nm.

51. The apparatus of claim 46, wherein the constraining dimension is in the range of about 1–2 nm.

52. The apparatus of claim 46, wherein the constraining dimension is located at the exit or entry port of the aperture.

53. The apparatus of claim 46, wherein the constraining dimension is located within the channel of the aperture.

54. The apparatus of claim 46, wherein the constraining dimension extends through the channel for a length that is in the range of 0.1 to 10 nm.

55. The apparatus of claim 46, wherein the constraining dimension extends through the channel for a length that is in the range of 0.1 to 5 nm.

56. The method of claim 46, wherein the solid-state substrate is selected from the group consisting of inorganic compounds, organic and inorganic polymers and glasses.

57. The method of claim 46, wherein the solid-state membrane has a thickness in the range of about 10 nm to about 1 mm.

58. The method of claim 46, wherein the solid-state membrane has a thickness in the range of about 50 nm to about 100 nm.

59. The method of claim 46, wherein the solid-state membrane has a capacitance of less than about 0.1 pF.

60. The method of claim 46, wherein polymer molecule interactions with the detector are detected as electronic currents at first and second electrodes adjacent to the aperture and in electrical communication with said channel.

61. The method of claim 60, wherein translational current is detected.

62. The method of claim 60, wherein current along the length of the channel is detected.

63. The method of claim 46, wherein polymer molecule interactions with the detector are detected as ionic conductance in the channel.

64. The method of claim 40, 60 or 63, wherein the amplitude of duration of individual conductance measurements is indicative of sequential identity of monomers of the polymer molecule.

65. The method of claim 40, 60 or 63, wherein the number of changes in the conductance measurement is an indication of the number of monomers in the polymer.

66. The method of claim 40, 60 or 63, wherein the duration of the individual conductance measurement is an indication of the number of monomers in the polymer molecule.

67. The method of claim 40, 60 or 63, wherein multiple molecules of a heterogeneous mixture of individual polymer molecules are characterized to provide a size distribution of polymers in the mixture.

68. The method of claim 46, wherein polymer molecule traverses the aperture by application of a voltage gradient or use of a biomotor.

69. The method of claim 46, wherein a polymer replicating catalyst is in contact with the aperture.

70. The method of claim 69, wherein polymer replicating catalyst is located adjacent to, below, above, or within the aperture.

71. The method of claim 46, wherein the constraining dimension comprises the detector.

72. A method for evaluating a polymer molecule, the polymer molecule including linearly connected monomer residues, comprising:
   providing a candidate hybridized polynucleotide molecule in a liquid;
   contacting a liquid containing a candidate hybridized polynucleotide molecule with an insulating solid-state membrane having an aperture therein, said aperture having a diameter insufficient to permit traversal of the hybridized molecule of the aperture;
   causing the candidate polymer molecule to traverse the aperture of the membrane, whereby the hybridized polymer molecule is denatured and the single-stranded polymer interacts sequentially with the aperture and data suitable to determine polymer molecule characteristics are obtained.

73. The method of claim 72, whereby the hybridized polymer molecule oscillates between a first condition at which the polymer can not advance into the aperture and a second condition at which the hybridized molecule is denatured and a single strand of the polymer advances into the aperture.

74. The method of claim 73, wherein the rate of oscillation between the first and second conditions is selected to advance the polymer by about a single monomer with each oscillation.

75. The method of claim 74, wherein the condition varied is an applied potential gradient across the membrane.

76. The method of claim 72, wherein the rate of traversal of a single strand DNA is an order of magnitude slower when using hybridized polymer than when using a single strand polymer.

* * * * *

UNITED STATES PATENT AND TRADEMARK OFFICE
CERTIFICATE OF CORRECTION

PATENT NO. : 6,627,067 B1                                    Page 1 of 1
DATED       : September 30, 2003
INVENTOR(S) : Branton et al.

It is certified that error appears in the above-identified patent and that said Letters Patent is hereby corrected as shown below:

Column 1,
Line 21, "grant no. N65236-99-1-5407" should be -- grant no. N65236-98-1-5407 --

Column 28,
Line 60, "a detector for detecting, sensing" should be -- a detector for sensing --
Lines 61 and 62, "molecule with the aperture detector" should be -- molecule with the detector --

Column 29,
Line 13, "range of about less than 0.1" should be -- range of about 0.1 --

Column 30,
Lines 9 and 10, "dimension diameter feature" should be -- dimension --

Signed and Sealed this

Seventeenth Day of February, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,627,067 B1
DATED : September 30, 2003
INVENTOR(S) : Branton et al.

It is certified that error appears in the above-identified patent and that said Letters Patent is hereby corrected as shown below:

<u>Title page,</u>
Item [75], Inventors, should be:

-- Daniel Branton, Lexington, MA (US); Jene A. Golovchenko, Lexington, MA (US); Timothy J. Denison, Andover, MA (US); Derek Stein, Somerville, MA (US); Jiali Li, Cambridge, MA (US) --

Signed and Sealed this

Twenty-third Day of November, 2004

JON W. DUDAS
*Director of the United States Patent and Trademark Office*